US008790871B2

(12) United States Patent
Spinale et al.

(10) Patent No.: US 8,790,871 B2
(45) Date of Patent: Jul. 29, 2014

(54) DETECTING DIASTOLIC HEART FAILURE BY PROTEASE AND PROTEASE INHIBITOR PLASMA PROFILING

(75) Inventors: Francis G. Spinale, Charleston, SC (US); Robert E. Stroud, Mt. Pleasant, SC (US); Michael R. Zile, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 1379 days.

(21) Appl. No.: 12/299,999

(22) PCT Filed: Apr. 24, 2007

(86) PCT No.: PCT/US2007/067292
§ 371 (c)(1),
(2), (4) Date: Mar. 22, 2009

(87) PCT Pub. No.: WO2007/133905
PCT Pub. Date: Nov. 22, 2007

(65) Prior Publication Data
US 2009/0221015 A1 Sep. 3, 2009

Related U.S. Application Data

(60) Provisional application No. 60/893,781, filed on Mar. 8, 2007, provisional application No. 60/798,953, filed on May 9, 2006.

(51) Int. Cl.
*G01N 33/68* (2006.01)
*G01N 33/573* (2006.01)
(52) U.S. Cl.
CPC .......... *G01N 33/573* (2013.01); *G01N 2800/50* (2013.01); *G01N 2800/325* (2013.01); *G01N 2333/96486* (2013.01)
USPC ................................ 435/5; 435/63; 435/7.92
(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,376,110 A | 3/1983 | David et al. |
| 4,452,901 A | 6/1984 | Gordon et al. |
| 5,424,000 A | 6/1995 | Winicov et al. |
| 2004/0121343 A1 | 6/2004 | Buechler |
| 2008/0171352 A1 | 7/2008 | Goix et al. |
| 2009/0005336 A1 | 1/2009 | Wang |
| 2010/0010073 A1 | 1/2010 | Thum |
| 2010/0267804 A1 | 10/2010 | Port |
| 2011/0117560 A1 | 5/2011 | Spinale |

FOREIGN PATENT DOCUMENTS

| | | |
|---|---|---|
| WO | 2004/059293 | 7/2004 |
| WO | 2007133905 | 11/2007 |
| WO | 2008008809 | 1/2008 |
| WO | 2008/085895 | 7/2008 |
| WO | 2010/031821 | 3/2010 |
| WO | 2010/054016 | 5/2010 |
| WO | 2012/065095 | 5/2012 |
| WO | 2012/065113 | 5/2012 |

OTHER PUBLICATIONS

Hua Li, MMP/TIMP expression in spontaneously hypertensive heart failure rats: the effect of ACE- and MMP-inhibition. Cardiovascular Research, vol. 46, Issue 2, pp. 298-306.*
Stroud et al. Plasma Monitoring of the Myocardial Specific Tissue Inhibitor of Metalloproteinase-4 After Alcohol Septal Ablation in Hypertrophic Obstructive Cardiomyopathy. Journal of Cardiac Failure vol. 11 No. 2 2005.*
Yun You Li, (Differential Expression of Tissue Inhibitors of Metalloproteinases in the Failing Human Heart Circulation 1998, 98:1728-1734).*
Francis G. Spinale Chronic Matrix Metalloproteinase Inhibition Following Myocardial Infarction in Mice: Differential Effects on Short and Long-Term Survival.*
Absi, et al., "Altered patterns of gene expression distinguishing ascending aortic aneurysms from abdominal aortic aneurysms: Complementary DNSA expression profiling in the molecular characterization of aortic disease", J Thorac Cardlovasc Surg., 126(2):344-57 (2003).
Ahmed, et al., "Matrix metalloproteinases/tissue inhibitors of metalloproteinases: Relationship between changes in proteolytic determinants of matrix composition and structural, functional and clinical manifestations of hypertensive heart desease", Circ., 113:2089-96 (2006).
Aime-Sempe, et al., "Myocardial cell death in fibrillating and dilated human right atria", J Am College of Cardiology, 34:1577-86 (1999).
Albinsson, et al., "MicroRNAs are necessary for vascular smooth muscle growth, differentiation, and function", Arterioscler Thromb Vasc Biol., 30(6):1118-26 (2010).
Alla, et al., "Early changes in serum markers od cardiac extra-cellular matrix turnover in patients with uncomplicated hypertension and type II diabetes", Eur J Heart Fail., 8(2):147-53 (2006).
Allessie, et al., "Electrical, contractile and structural remodeling during atrial fibrillation", Cardiovasc Res, 54:230-40 (2002).
Allessie, et al., "Pathophysiology and prevention of atrial fibrillation", Circ.,103:769-77 (2001).
Altieri, et al. "Metalloproteinases 2 and 9 are increased in plasma of patients with heart failure", Eur J of Clin Invest, 33:648-56 (2003).
Ambros, et al., "MicroRNAs and other tiny endogenous RNAs in *C. elegans*", Curr. Biol., 13(10):807-18 (2003).

(Continued)

*Primary Examiner* — Kagnew H Gebreyesus
(74) *Attorney, Agent, or Firm* — Meunier Carlin & Curfman, LLC

(57) ABSTRACT

Disclosed herein are methods of detecting and predicting diastolic heart failure and predicting congestive heart failure comprise protease and protease inhibitor profiling.

15 Claims, 11 Drawing Sheets

(56) References Cited

OTHER PUBLICATIONS

Ausma, et al., "Reverse structural and gap-junctional remodeling after prolonged atrial fibrillation in the goat", Circulation, 107:2051-8 (2003).

Ausma, et al., "Structural changes of atrial myocardium due to sustained atrial fibrillation in the goat", Circulation, 96:3157-63 (1997).

Ausma, et al., "Time course of atrial fibrillation-induced cellular structural remodeling in atria of the goat", J Mol Cell Cardiol, 33:2083-94 (2001).

Baker, et al., "Metalloproteinase inhibitors: biological actions and therapeutic opportunities", J Cell Sci., 1115 (Pt 19):3719-27 (2002).

Bartel, "MicroRNAs: genomics, biogenesis, mechanism, and function", Cell, 116(2):281-97 (2004).

Bartel, "MicroRNAs: target recognition and regulatory functions", Cell, 136(2):215-33 (2009).

Benjamin, et al., "Impact of atrial fibrillation on the risk of death: the Framingham Heart Study", Circulation, 98:946-52 (1998).

Blankenberg, et al., "Plasma Concentrations and Genetic Variation of Matrix Metalloproteinase 9 and Prognosis of Patients With Cardiovascular Disease", Circulation, 107:1579-85 (2003).

Boldt, et al., "Fibrosis in left atrial tissue of patients with atrial fibrillation with and without underlying mitral valve disease", Heart, 90:400-05 (2004).

Bollmann, et al., "Atrial fibrillatory frequency predicts atrial defibrillation threshold and early arrhythmia recurrence in patients undergoing internal cardioversion of persistent atrial fibrillation", Pacing Clin Etectrophysiol, 25:1179-84 (2002).

Borden, et al., "Transcriptional control of matrix metalloproteinases and the tissue inhibitors of matrix metalloproteinases", Crit Rev Eukaryot Gene Exp, 7:159-78 (1997).

Borges, et al., "Tissue diffusion and retention of metalloproteinases in ascending aortic aneurysms and dissections", Human pathology., 40(3):306-13 (2009).

Boyum, et al., "Matrix metalloproteinase activity in thoracic aortic aneurysms associated with bicuspid and tricuspid aortic valves", J Thorac Cardiovasc Surg., 127(3):686-91(2004).

Brundel, et al., "Molecular mechanisms of remodeling in human atrial fibrillation", Cardiovascular Res, 54:315-24 (2002).

Chareonthaitawee, et al., "Relation of initial infarct size to extent of left ventricular remodeling in the year after acute myocardial infarction", J Am Coil Cardiol, 25:567-73 (1995).

Chen, et al., "Characterization of microRNAs in serum: a novel class of biomarkers for diagnosis of cancer and other diseases", Cell Res., 18:997-1006 (2008).

Chung, et al., "Loss of elastic fiber integrity and reduction of vascular smooth muscle contraction resulting from the upregulated activities of matrix metalloproteinase-2 and -9 in the thoracic aortic aneurysm in Marfan syndrome", Circ Res.,101(5):512-22 (2007).

Coker, et al., "Matrix metalloproteinase expression and activity in isolated LV myocyte preparations following neurohormonal stimulation", Am J Physiol, 281:H543-H551 (2001).

Creemers, et al., "Deficiency of TIMP-1 exacerbates LV remodeling after myocardial infarction in mice", Am J Physiol, 284:H364-371 (2002).

Crowther, "ELISA: Theory and Practice," Methods Mol Biol, 42:1-218 (1995).

Damodarasamy, et al., "Collagen Extracts Derived From Young and Aged Mice Demonstrate Different Structural Properties and Cellular Effects in Three-Dimensional Gels", J Gerontol A Biol Sci Med Sci., 65(3):209-18 (2010).

Deisenhofer, et al., "Circumferential mapping and electric isolation of pulmonary veins in patients with atrial fibrillation", Am J Cardiology, 91:159-63 (2003).

Dispersyn, et al., "Cardiomyocyte remodelling during myocardial hibernation and atrial fibrillation: prelude to apoptosis", Cardiovasc Res, 43:947-57 (1999).

Divakaran and Mann, "The Emerging Role of MicroRNAs in Cardiac Remodeling and Heart Failure", Ciro Res., 103:1072-83 (2008).

Dong, et al., "MicroRNA Expression Signature and the Role of MicroRNA-21 in the Early Phase of Acute Myocardial Infarction", J Biol Chem., 284(43):29514-25 (2009).

Ducharme, et al., "Targeted deletion of matrix metalloproteinase-9 attenuates left ventricular enlargement and collagen accumulation after experimental myocardial infarction", J Clin Invest, 106:55-62 (2000).

Duisters, et al., "miR-133 and miR-30 Regulate Connective Tissue Growth Factor. Implications for a Role of MicroRNAs in Myocardial Matrix Remodeling", Circ Res, 104:170-8 (2009).

Elia, et al., "The knockout of miR-143 and -145 alters smooth muscle cell maintenance and vascular homeostasis in mice: correlates with human disease", Cell Death Differ., 16(12):1590-98 (2009).

Erlebacher, et al., "Early dilation of the infarcted segment in acute transmural myocardial infarction: role of infarct expansion in acute left ventricular enlargement", J Am Coil Cardiol, 4(2)201-8 (1984).

Esteve, et al., "Protein kinase C-zeta regulates transcription of the matrix metalloproteinase-9 gene induced by IL-i and TNF-alpha in glioma cells via NF-kappa B", J Biol Chem, 277(38):35150-5 (2002).

Etoh, et al., "Myocardial and interstitial matrix metalloproteinase activity after acute myocardial infarction in pigs", Am J Physiol Heart Circ Physiol, 281:H987-H994 (2001).

Falcone, et al., "Plasma Levels of Soluble Receptor for Advanced Glycation End Products and Coronary Artery Disease in Nondiabetic Men", Arterioscler Thromb Vasc Biol, 25:1032-7 (2005).

Felkin, et al., "A quantitative gene expression profile of matrix metalloproteinases (MMPS) and their inhibitors (TIMPS) in the myocardium of patients with deteriorating heart failure requiring left ventricular assist device support", J Heart Lung Transpl., 25:1413-19 (2006).

Fini, et al., "Regulation of matrix metalloproteinase gene expression", Matrix Metalloproteinases. San Diego: Academic, 299-356, (1998).

Fragakis, et al., "Reversion and maintenance of sinus rhythm in patients with permanent atrial fibrillation by internal cardioversion followed by biatrial pacing", Pacing Clin Electrophysiol 25:278-86 (2002).

Frick, et al., "Factors predicting success rate and recurrence of atrial fibrillation after first electrical cardioversion in patients with persistent atrial fibrillation", Clin Cardiol, 24:238-44 (2001).

Friedman, et al., "Most mammalian mRNAs are conserved targets of microRNAs", Genome Res. 19(1):92-105 (2009).

Frustaci, et al., "Histological Substrate of Atrial Biopsies in Patients With Lone Atrial Fibrillation", Circulation, 96:1180-4 (1997).

Goette, et al., "Calpains and cytokines in fibrillating human atria", Am J Physiol Heart Circ Physiol, 283:H264-H272 (2002).

Goldberg, et al., "Human 72-kilodalton type IV collagenase forms a complex with a tissue inhibitor of metalloproteinase designated TIMP", PNAS, 86:8207-11 (1989).

Grimson, et al., "MicroRNA targeting specificity in mammals: determinants beyond seed pairing", Mol Cell., 27(1):91-105 (2007).

Grishok, et al., "Genes and mechanisms related to RNA interference regulate expression of the small temporal RNAs that control *C. elegans* developmental timing", Cell, 106(1):23-34 (2001).

Gross, et al., "Collagenolytic activity in amphibian tissues: a tissue culture assay", PNAS,48:1014-22 (1962).

Gunja-Smith, et al., "Remodeling of human myocardial collagen in idiopathic dilated cardiomyopathy: role of metalloproteinases and pyridinoline cross links", Am J Path, 148:1639-48 (1996).

Haro, et al., "Matrix metalloproteinase-7 dependent release of tumor necrosis factor alpha in a model of herniated disc resorption", J Clin Invest 105:143-50 (2000).

Herman, et al., "Expression of neutrophil collagenase (matrix metalloproteinase-8) in human atheroma: a novel collagenolytic pathway suggested by transcriptional profiling", Circulation 104;1878-80 (2001).

Heymans, et al., "Inhibition of plaminogen activators or matrix metalloproteinases prevents cardiac rupture but impairs therapeutic angiogenesis and causes cardiac failure", Nature Med 5:1135-42 (1999).

(56) References Cited

OTHER PUBLICATIONS

Hirohata, et al., "Time dependent alterations of serum matrix metalloproteinase-1 and metalloproteinase-1 tissue inhibitor after successful reperfusion of acute myocardial infarction", Heart, 78:278-84 (1997).
Hobbs, et al., "Reversal of atrial electrical remodeling after cardioversion of persistent atrial fibrillation in humans", Circulation, 101:1145-51 (2000).
Hofmann, et al., "RAGE mediates a novel proinflammatory axis: a central cell surface receptor for S100/calgranulin polypeptides", Cell, 97:889-901(1999).
Holmbeck, et al., "MT1-MMP: a tethered collagenase", J Cell Physiol, 200:11-9 (2004).
Hunt, et al., "The amino-terminal portion of pro-brain natriuretic peptide (Pro-BNP) circulates in human plasma", Biochem Biophys Res Commun. 214:1175-83 (1995).
Ikonomidis, et al., "Effects of deletion of the matrix metalloproteinase 9 gene on development of murine thoracic aortic aneurysms", Circulation, 112(9 Suppl):I242-8 (2005).
Ikonomidis, et al., "Expression of matrix metalloproteinases and endogenous inhibitors within ascending aortic aneurysms of patients with bicuspid or tricuspid aortic valves", J Thorac Cardiovasc Surg. 133(4):1028-36 (2007).
Ikonomidis, et al., "Expression of matrix metalloproteinases and endogenous inhibitors within ascending aortic aneurysms of patients with Marfan syndrome", Circulation., 114(1 Suppl):I365-70 (2006).
Inokubo, et al., "Plasma levels of matrix metalloproteinase-9 and tissue inhibitor of metalloproteinase-1 are increased in the coronary circulation in patients with acute coronary syndrome", Am Heart J, 141:211-7 (2001).
Isselbacher, "Thoracic and abdominal aortic aneurysms", Curr., 111 (6):816-28 (2005).
Jones, et al., "Alterations in membrane type-1 matrix metalloproteinase abundance after the induction of thoracic aortic aneurysm in a murine model", Am J Physiol Heart Circ Physiol. 299(1):H114-24 (2010).
Jones, et al., "Selective microRNA suppression in human thoracic aneurysms: relationship of miR-29a to aortic size and proteolytic induction", Circ Cardiovasc Genet, 4(6):605-13 (2011).
Jones, et al., "Spatiotemporal expression and localization of matrix metalloproteinase-9 in a murine model of thoracic aortic aneurysm", J Vasc Surg., 44(6):1314-21(2006).
Kaden, et al., "Time dependent changes in the plasma concentration of matrix metalloproteinase 9 after acute myocardial infarction", Cardiology, 99:140-4 (2003).
Kalousova, et al., "Receptor for advanced glycation end products soluble form and gene polymorphisms in chronic haemodialysis patients", Neprol Dial, Jul. 2007;22 (7) :2020-6. Epub Mar. 2007.
Kostin, et al., "Structural correlate of atrial fibrillation in human patients", Cardiovas.Res., 54:361-79 (2002).
Kozomara, et al., "miRBase: integrating microRNA annotation and deep-sequencing data", Nucleic Acids Res., 39(Database issue):D152-157 (2011).
Lagos-Quintana, et al., "Identification of novel genes coding for small expressed RNAs", Science, 294(5543):853-8 (2001).
Lakatta and Levy, "Arterial and cardiac aging: major shareholders in cardiovascular disease enterprises: Pt I: aging arteries: a "set up" for vascular disease", Circulation,107(1):139-46 (2003).
Lau, et al., "An abundant class of tiny RNAs with probable regulatory roles in *Caenorhabditis elegans*", Science, 294(5543):858-62 (2001).
Lee and Ambros, "An extensive class of small RNAs in *Caenorhabditis elegans*", Science, 294(5543):862-4 (2001).
Lellouche, et al., "Usefulness of plasma B-type natriuretic peptide in predicting recurrence of atrial fibrillation one year after external cardioversion", Am J Cardiol ,95:1380-82 (2005).
Lemaire, et al., "Matrix metalloproteinases in ascending aortic aneurysms: bicuspid versus trileaflet aortic valves", J Surg Res,123(1):40-8 (2005).

Lewis, et al., "Conserved seed pairing, often flanked by adenosines, indicates that thousands of human genes are microRNA targets", Cell., 120(1)15-20 (2005).
Li, et al., "Attenuation of micro-RNA-1 derepresses the cytoskeleton regulatory protein twinfilin-1 to provoke cardiac hypertrophy", J Cell Sci., 123(pt14):2444-52 (2010).
Li, et al., "Matrilysin shedding of syndecan-1 regulates chemokine mobilization and transepithelial efflux of neutrophils in acture lung injury", Cell ,111:635-46 (2002).
Li, et al., "Proinflammatory cytokines regulate tissue inhibitors of metalloproteinases and disintegrin metalloproteinase in cardiac cells", Cardiovasc Res., 42(1):162-72 (1999).
Li, et al., "Real-Time Polymerase Chain Reaction MicroRNA Detection Based on Enzymatic Stem-Loop Probes Ligation", Anal Chem., 1:81(13):5446-51 (2009).
Li and Wong, "Model-based analysis of oligonucleotide arrays: expression index computation and outlier detection", PNAS, 98(1):31-6 (2001a).
Liao, et al., "A microRNA profile comparison between thoracic aortic dissection and normal thoracic aorta indicates the potential role of microRNAs in contributing to thoracic aortic dissection pathogenesis", J Vasc Surg., 53(5):1341-9.e3 (2011).
Liao, et al.,"Cardiotrophin-1 (CT-1) can protect the adult heart from injury when added both prior to ischaemia and at reperfusion", Cardiovasc. Res., 53:902-10 (2002).
Lin, et al., "Predictors of clinical recurrence after successful electrical cardioversion of chronic persistent atrial fibrillation: clinical and electrophysiological observations", Cardiol., 97:133-7 (2002).
Liu, et al., "Identification and characteristics of microRNAs with altered expression patterns in a rat model of abdominal aortic aneurysms", Tohoku J Exp Med., 222(3):187-93 (2010).
Liu, et al., "microRNA-133a regulates cardiomyocyte proliferation and suppresses smooth muscle gene expression in the heart", Genes Dev., 22(23):3242-54 (2008).
Liu, et al., "Renal medullary microRNAs in Dahl salt-sensitive rats: miR-29b regulates several collagens and related genes", Hypertension, 55(4):974-82 (2010b).
Longo, et al., "Matrix metalloproteinases 2 and 9 work in concert to produce aortic aneurysms", J Clin Invest. 110(5):625-32 (2002).
Mair, et al., "The impact of cardiac natriuretic peptide determination on the diagnosis and management of heart failure", Clin Chem Lab Med., 39:571-88 (2001).
Marin, et al., "Is Thrombogenesis in Atrial Fibrillation Related to Matrix Metalloproteinase-1 and Its Inhibitor, TIMP-1", Stroke,34:1181-6 (2003).
Matrisian, "Metalloproteinases and their inhibitors in matrix remodeling", Trends in Genetics, 6:121-5 (1990).
McMillan, et al., "In situ localization and quantification of mRNA for 92-kD type IV collagenase and its inhibitor in aneurysmal, occlusive, and normal aorta", Arterioscler Thromb Vasc Biol. 15(8):1139-44 (1995a).
McMillan, et al., "In situ localization and quantification of seventy-two-kilodalton type IV collagenase in aneurysmal, occlusive, and normal aorta", J Vasc Surg, 22(3):295-305 (1995b).
Mitchell, et al., "Circulating microRNAs as stable blood-based markers for cancer detection", PNAS, 105(30)10513-8 (2008).
Montaner, et al., "Matrix Metalloproteinase Expression is Related to Hemorrhagic Transformation After Cardioembolic Stroke", Stroke, 32:2762-7 (2001b).
Montaner, et al., "Matrix metalloproteinase-9 pretreatment level predicts intracranial hemorrhagic complications after thrombolysis in human stroke", Circ, 107:598-603 (2003).
Montaner , et al.. "Matrix Metalloproteinase Expression After Human Cardioembolic Stroke: Temporal Profile and Relation to Neurological Impairment", Stroke, 32:1759-66 (2001).
Moon, et al., "ERK1/2 mediates TNF-alpha induced matrix metalloproteinase-9 expression in human vasuclar smooth muscle cells via the regulation of NF-kappaB and AP-1: Involvement of the ras dependent pathway", J Cell Physiol., 198:417-27 (2004).
Mukherjee, et al., "Myocardial infarct expansion and matrix metalloproteinase inhibition", Circulation, 107(4):618-25 (2003).
Nagase, "Activational mechansims of matrix metalloprteinases", Biol Chem., 378:151-60 (1997).

(56) References Cited

OTHER PUBLICATIONS

Peterson, et al., "Matrix metalloproteinase inhibition attenuates left ventricular remodeling and dysfunction in a rat model of progressive heart failure", Circ,103(18): 2303-9 (2001).
Pfeffer, et al., "Ventricular remodeling after myocardial infarction. Experimental observations and clinical implications", Circ., 81:1161-72 (1990).
Pozzoli, et al., "Predictors of primary atrial fibrillation and concomitant clinical and hemodynamic changes in patients with chronic heart failure: a prospective study in 344 patients with baseline sinus rhythm", J Am Coll Cardiol., 32:197-204 (1998).
Psaty, et al., "Incidence of and risk factors for atrial fibrillation in older adults", Circ., 96:2455-61 (1997).
Qin and Zhang, "MicroRNAs in vascular disease", J Cardiovasc Pharmacol., 57(1):8-12 (2011).
Rohde, et al., "Matrix metalloproteinase inhibition attenuates early left ventricular enlargement after experimental myocardial infarction in mice", Circ, 99:3063-70 (1999).
Roy, et al., "MicroRNA expression in response to murine myocardial infarction: miR-21 regulates fibroblast metalloprotease-2 via phosphatase and tensin homologue", Cardiovaso Res., 82(1):21-9 (2009).
Sanfilippo, et al., "Atrial enlargement as a consequence of atrial fibrillation. A prospective echocardiographic study", Circ., 82:792-7 (1990).
Sawicki, et al., "Release of gelatinase a during platelet activation mediates aggregation", Nature, 386;616-9 (1997).
Schleicher, et al., "Increased accumulation of the glycoxidation product N (epsilon)-(carboxymethyl)lysine in human tissues in diabetes and aging", J. Clin. Invest. , 99(3):457-68 (1997).
Schotten, et al., "Cellular mechanisms of depressed atrial contractility in patients with chronic atrial fibrillation", Circ., 103: 691-8 (2001).
Schotten, et al., "Electrical and contractile remodeling during the first days of atrial fibrillation go hand in hand", Circ., 107:1433-9 (2003).
Schulz-Menger, et al., "The value of magnetic resonance imaging of the left ventricular outflow tract in patients with hyupertrophic obstructive cardiomyopahty after septal artery embolization", Circ., 101:1764-6 (2000).
Schulze, et al., "Imbalance between tissue inhibitor of metalloproteinase-4 and matrix metalloproeinases during acute myocardial ischemia-reperfusion injury", Circ, 107:2487-92 (2003).
Schwartz, et al., "Impact of pre-existing conditions, age and the length of cardiopulmonary bypass on postoperative outcome after repair of the ascending aorta and aortic arch for aortic aneurysms and dissections", Interact Cardiovasc. Thorac Sug., 7(5):850-4 (2008).
Schwartzkopff, et al., "Elevated serum markers of collagen degradation in patients with mid to moderate dilated cardiomyopathy", Eur. J Heart Fail., 4:439-44 (2002).
Sen, et al., "Micromanaging vascular biology: tiny microRNAs play big band", J Vasc Res., 46(6):527-40 (2009).
Sheng, et al., "Cardiotrophin-1 displays early expression in the murine heart tube and promotes cardiac myocyte survival", Development, 122:419-28 (1996).
Shirwany, et al., "Extracellular matrix remodeling in hypertensive heart disease", J of Am College of Cardiology, 48:97-98 (2006).
Sinha, et al., "A biologic basis for asymmetric growth in descending thoracic aortic aneurysms: a role for matrix metalloproteinase 9 and 2", J Vasc Surg., 43(2):342-8 (2006).
Siwik, et al., "Oxidative stress regulates collagen synthesis and matrix metalloproteinase activity in cardiac fibroblasts", Am J Phys., 280:C53-60 (2001).
Small, et al., "MicroRNAs Add a New Dimension to Cardiovascular Disease", Circ., 121:1022-32 (2010).
Spinale, et al., "Extracellular degradative pathways in myocardial remodeling and progression to heart failure", J Cardiac Failure, 8:S332-8 (2002).
Spinale, et al., "Matrix metalloporeinase inhibition during developing congestive heart failure in pigs: effects on left ventricular geometry and function", Circ Res, 85:364-76 (1999).
Spinale, et al., "Time-dependent changes in matrix metalloproteinase activity and expression during the progression of congestive heart failure: relation to ventricular and myocyte function", Circ. Res., 82(4):482-95 (1998).
St. John Sutton, et al., "Quantitative two-dimensional echocardiographic measurements are major predictors of adverse cardiovascular events after myocardial infarction. The protective effects of captopril", Circ., 89;68-75 (1994).
Steele, et al., "MBP-1 upregulates miR-29b that represses Mcl-1, collagens, and matrix-metalloproteinase-2 in prostate cancer cells", Genes Cancer, 1(4):381-7 (2010).
Tamarina, et al., "Expression of matrix metalloproteinases and their inhibitors in aneurysms and normal aorta", Surgery, 122(2):264-71; discussion 271-262 (1997).
Thijssen, et al., "Structural remodelling during chronic atrial fibrillation: act of programmed cell survival", Cardiovas Res, 52:14-24 (2001).
Thomas, et al., "Increased matrix metalloproteinase activity and selective upregulation inLV myocardium from patients with end-stage dilated cardiomyopathy", Circ, 97:1708-15 (1998).
Todd, et al., "Prevalence and significance of focal sources of atrial arrhythmia in patients undergoing cardioversion of persistent atrial fibrillation", J Cardiovasc Electrophysiol., 11:616-22 (2000).
Tziakes, et al., "N-terminal pro-B-type natriuretic peptide and matrix metalloproteinases in early an dlate left ventricular remodeling after acute myocardial infarction", Am J Cardio., 96:31-4 (2005).
Van Gelder, et al., "Prediction of uneventful cardioversion and maintenance of sinus rhythm from direct-current electrical cardioversion of chronic atrial fibrillation and flutter", Am J Cardiol. 68:41-6 (1991).
van Rooij, et al. "Dysregulation of microRNAs after myocardial infarction reveals a role of miR-29 in cardiac fibrosis", PNAS, 105(35):13027-32 (2008).
Vincenti, "The matrix metalloproteinase (MMP) and tissue inhibitor of metalloproteinase (TIMP) genes. Transcriptional and post-transcriptional regulation, signal transduction and cell-type-specific expression", Methods Mol Biol., 151:121-48 (2001).
Visse, et al., "Matrix metalloproteinases and tissue inhibitors of metalloproteinases: structure, function, and biochemistry", Circ Res., 92:827-39 (2003).
Wautier, et al., "Receptor-mediated endothelial cell dysfunction in diabetic vasculopathy. Soluble receptor for advanced glycation end products blocks hyperpermeability in diabetic rats", J. Clin. Invest. 97:238-43 (1996).
Wazni, et al., "C reactive protein concentration and recurrence of atrial fibrillation after electrical cardioversion", Heart, 91:1303-5 (2005).
Webb, et al., "Specific temporal profile of matrix metalloproteinase release occurs in patients after myocardial infarction: relation to left ventricular remodeling", Circulation, 114(10):1020-27 (2006).
White, et al., "Left ventricular end-systolic volume as the major determinant of survival after recovery from myocardial infarction", Circ., 76(1):44-51 (1987).
Wilson, et al., "Region and type-specific induction of matrix metalloproteinases occurs with post-myocardial infarction remodeling", Circ., 107(22):2857-63 (2003).
Woessner, et al., "The matrix metalloproteinase family", Matrix metalloproteinases. Parks WC, Mecham RP, eds. Academic Press, San Diego. Ppl-14 (1998).
Wyse, et al. "A Comparison of Rate Control and Rhythm Control in Patients with Atrial Fibrillation", N Engl J Med ., 347:1825-33 (2002).
Xu, et al., "The *Drosophila* microRNA Mir-14 suppresses cell death and is required ior normal fat metabolism", Curr. Biol., 13(9):790-5 (2003).
Yang, et al., "Advances in diastolic heart failure", World J Cardiol., 2(3):58-63 (2010).
Yu, et al., "Reversal of atrial electrical remodeling following cardioversion of long-standing atrial fibrillation in man", Cardiovas. Res., 42:470-6 (1999).
Zhong, et al., "Changes in metalloproteinase and tissue inhibitor of metalloproteinase during tachycardia-induced cardiomyopathy by rapid atrial pacing in dogs", Cardiology, 106:22-8 (2006).

(56) References Cited

OTHER PUBLICATIONS

Anderson, L and Anderson, NG. High resolution two-dimensional electrophoresis of human plasma proteins, Proc. Natl. Acad. Sci. 74:5421-5425 (1977).
Bigg, HF, et al. Tissue inhibitor of metalloproteinase-4 inhibits but does not support the activation of gelatinase A via efficient inhibition of membrane type 1-matrix metalloproteinase. Cancer Res 2001; 61(9): 3610-8.
Bradham, WS, et al. Release of matrix metalloproteinases following alcohol septal ablation in hypertrophic obstructive cardiomyopathy. JACC 2002; 40(12): 2165-73.
Brew K, et al. Tissue inhibitors of metalloproteinases: evolution, structure and function. Biochimica et Biophysica Acta. 2000; 1477:267-283.
Butler, J. E., In: Structure of Antigens, vol. 1 (Van Regenmortel, M., CRC Press, Boca Raton, 1992, pp. 209-259.
Butler, J. E., In: van Oss, C. J. et al., (eds), Immunochemistry, Marcel Dekker, Inc., New York, 1994, pp. 759-803.
Butler, J. E., The amplified ELISA: principles of and applications for the comparative quantitation of class and subclass antibodies and the distribution of antibodies and antigens in biochemical separates. Meth. Enzymol. 73:482-523 (1981).
Caterina, NCM, et al. Glycosylation and NH2-terminal domain mutant of tissue inhibitor of metalloproteinases-1 (TIMP-1). Biochem Biophys Acta 1998; 1388: 21-34.
Chapman, RE and Spinale, FG. Extracellular protease activation and unraveling of the myocardial interstitium: critical steps toward clinical applications. Am J Physiol. 2004;286;H1-H10.
Chobanian, AV, et al. National Heart, Lung, and Blood Institute Joint National Committee on Prevention, Detection, Evaluation, and Treatment of High Blood Pressure; National High Blood Pressure Education Program Coordinating Committee. The Seventh Report of the Joint National Committee on Prevention, Detection, Evaluation, and Treatmetn of High Blood Pressure; the JNC 7 report. JAMA. 2003;289:2560-72.
Creemers, EEJM, et al. Matrix metalloproteinase inhibition after myocardial infarction. A new approach to prevent heart failure? Circulation Res 2001; 89; 201-210.
Dennis, JW, et al. Protein glycosylation in development and disease. BioEssays 1999; 21: 412-421.
Deschamps, AM, et al. Myocardial interstitial matrix metalloproteinase activity is altered by mechanical changes in LV load: interaction with the angiotensin type 1 receptor. Circ Res. 2005;27;96:1110-8.
Devereux, RB, et al. Echocardiographic assessment of left ventricular hypertrophy: comparison to necropsy findings. Am J Cardiol. 1986;57:450-8.
Diez J, et al. Losartan-dependent regression of myocardial fibrosis is associated with reduction of left ventricular chamber stiffness in hypertensive patients. Circulation. 2002;105:2512-2517.
Douglas, Da, et al. Computational sequence analysis of the tissue inhibitor of metalloproteinase family. J. Protein Chem 1997, 16:237-255.
Edwards, DR, et al. The roles of tissue inhibitors of metalloproteinases in tissue remodeling and cell growth. Int J Obes 1996: 20: S9-S15.
Galis, ZS and Khatri JJ. Matrix metalloproteinases in vascular remodeling and atherogenesis: the good, the bad and the ugly. Circ Res 2002; 90: 251-62.
Goffin, F, et al. Expression pattern of metalloproteinases and tissue inhibitor of matrix metalloproteinases in cycling human endometrium. Bio Reprod 2003.
Gomez, DE, et al. Tissue inhibitor of metalloproteinases: structure, regulation, and biological functions. EJCB 1997, 74: 111-112.
Greene, J, et al. Molecular cloning and characterization of human tissue inhibitor of metalloproteinase 4. J Biol Chem 1996; 271: 30375-30380.
Gunasinghe, SK, et al. Contributory role of matrix metalloproteinases in cardiovascular remodeling. Cardiovasc Heamat Disorders, 1(2) 75-91, 2001 Nagase H. Activational mechanisms of matrix metalloproteinases. Biological Chemistry 1997; 378: 151-160.
Hojo, Y, et al. Expression of matrix metalloproteinases in patients with acute myocardial infarction. Jpn Circ J 2001; 65; 71-75.
Joffs, C, et al. Cardiopulmonary bypass induces the synthesis and release of matrix metalloproteinases. Ann Thorac Surg. 2001; 71:1518-23.
Kai, H, et al. Peripheral blood levels of matrix metalloproteinases-2 and -9 are elevated in patients with acute coronary syndromes. J Am Coll Cardiol 1998; 32: 368-372.
Kenchaiah ,S and Pfeffer, MA. Cardiac remodeling in systemic hypertension. Med Clin North Am. 2004; 88:115-130.
Laemmli, U.K., Cleavage of structural proteins during the assembly of the head of bacteriophage T4, Nature 227:680 (1970).
Laviades, C, et al. Abnormalities of the extracellular degradation of collagen type I in essential hypertension. Circulation. 1998; 98:535-540.
Levy, D, et al. The progression from hypertension to congestive heart failure. JAMA. 1996; 275: 1557-1562.
Li, YY, et al. Differential expression of tissue inhibitors of metalloproteinases in the failing human heart. Circulation 1998, 98: 1728-1734.
Li, YY, et al. Downregulation of matrix metalloproteinases and reduction in collagen damage in the failing human heart after support with left ventricular assist devices. Circulaton 2001; 104: 1147-52.
Li-Saw-Hee, FL, et al. Lip GYH: Matrix metalloproteinase-9 and tissue inhibitor metalloproteinase-1 levels in essential hypertension. Relationship to left ventricular mass and anti-hypertensive therapy. Int J Cardiol. 2000; 75:43-47.
Lindsay, MM, et al. TIMP-1. A marker of left ventricular diastolic dysfunction and fibrosis in hypertenstion. Hypertension. 2002;40:136-141.
Lindsey, ML, et al. Extracellular matrix remodeling following myocardial injury. Ann Med. 2003;35:316-326.
Liu, YE, et al. Preparation and characterization of recombinant tissue inhibitor of metalo[roteinase 4. Am Soc Biochem Mol Biol 1997, 272: 20479-20483.
Lloyd-Jones, DM, et al. Lifetime risk for developing congestive heart failure. The Framingham Study. Circulation. 2002;106:3068-3072.
Lopez, B, et al. Biochemical assessment of myocardial fibrosis in hypertensive heart disease. Hypertension. 2001b;38:1222-1226.
Lopez, B, et al. Usefulness of serum carboxy-terminal propeptide of procollagen type I in assessment of the cardioreparative ability in antihypertensive treatment in hypertensive patients. Circulation. 2001a;104:286-291.
Maron, BJ. Hypertrophic cardiomyopathy: a systematic review. JAMA 2002; 13: 287(1308-1320).
Matsudiara, PT and Burgess, DR, SDS microslab linear gradient polyacrylamide gel electrophoresis, Anal. Biochem. 87:386-396 (1987).
Nagueh, SF, et al. Changes in left ventricular diastolic function 6 months after nonsurgical septal reduction therapy for hypertrophic obstructive cardiomyopathy. Circulation 1999: 99:344-347.
Nagueh, SF, et al. Changes in left ventricular filling and left atrial function six months after nonsurgical septal reduction therapy for hypertrophic obstructive cardiomyopathy. J Am Coll Cardiol 1999; 34: 1123-1128.
Nagueh, SF, et al. Decreased expression of tumor necrosis factor-alpha and regression of hypertrophy after nonsurgical septal reduction therapy for patients with hypertrophic obstructive cardiomyopathy. Circulation 2001; 103(14): 1844-50.
Nagueh, SF, et al. Doppler estimation of left ventricular filling pressure in sinus tachycardia. A new application of tissue Doppler imaging. Circulation. 1998; 98:1644-1650.
Neuhoff, et al. Improved staining of proteins in polyacrylamide gels including isoelectric focusing gels with clear background at nanogram sensitivity using Coomassie Brilliant Blue G-250 and R-250. Electrophoresis 9:255-262 (1988).
Neuhoff, et al., Clear background and highly sensitive protein staining with Coomassie Blue dyes in polyacrylamide gels: A systematic analysis. Electrophoresis 6:427-448 (1985).

(56) References Cited

OTHER PUBLICATIONS

O'Farrell, P.H. High Resolution Two-dimensional Electrophoresis of Proteins, J. Biol. Chem. 250:4007-4021 (1975).
Ornstein, L. Disc electrophoresis—I: Background and Theory, Ann. N.Y. Acad. Sci. 121:321-349 (1964).
Parsons, SL, et al. Matrix metalloproteinases. Brit J Surg 1997;84:160-166.
Peterson, JT, et al. Evolution of matrix metalloproteinase and tissue inhibitor expression during heart failure progression in the infracted rat. Cardiovas Res 2000; 46: 307-315.
Radomski, A, et al. Identification, regulation and role of tissue inhibitor of metalloproteinases-4 (TIMP-4) in human platelets. Br J Pharmaco, 2002; 137(8): 1130-1338.
Sahn, DJ, et al. Recommendations regarding quantitation in M-mode echocardiography: results of a survey of echocardiographic measurements. Circulation. 1978; 58: 1072-1083.
Schillaci, G., et al. Prognostic significance of left ventricular diastolic dysfunction in essential hypertension. J Am Coll Cardiol. 2002;39:2005-2011.
Schiller, NB, et al. Recommendations for quantitation of the left ventricle by two-dimensional echocardiography. American Society of Echocardiography Committee on Standards, Subcommittee on Quantitation of Two-Dimensional Echocardiograms. J Am Soc Echocardiography. 1989; 2: 358-367.
Sharp, PS, et al. Serum levels of low molecular weight advanced glycation end products in diabetic subjects. Diabet Med 2003; 20(7): 575-9.
Spencer, WH 3rd and Roberts R. Alcohol septal ablation in hypertrophic obstructive cardiomyopathy: the need for a registry. Circulation 2000; 102: 600-01.
Spinale, FG, et al. A matrix metalloproteinase induction/activation system exists in the human left ventricular myocardium and is upregulated in heart failure. Circulation 2000; 102; 1944-1949.
Spinale, FG. Matrix metalloproteinases. Regulation and dysregulation in the failing heart. Circ. Res. 2002;90:520-530.
Steinberg, TH, et al. Rapid and simple single nanogram detection of glycoproteins in polyacrylamide gels on electroblots. Proteomics 2001; 1(7): 841-55.
Stroud, RE, et al. Plasma monitoring of the myocardial specific tissue inhibitor of metalloproteinase-4 after alcohol septal ablation in hypertrophic obstructive cardiomyopathy. J Card Fail. 2005; 11:124-30.
Sundström, J. et al., Relations of plasma matrix metalloproteinase-9 to clinical cardiovascular risk factors and echocardiographic left ventricular measures: the Framingham Heart Study; Circulation 2004;109(23):2850-2856.
Tayebjee, MH, et al. Matrix metalloproteinase-9 and tissue inhibitor of metalloproteinase-1 in hypertension and their relationship to cardiovascular risk and treatment: a substudy of the Anglo-Scandinavian Cardiac Outcomes Trial (ASCOT). Am J Hypertens. 2004;17:764-9.
Tayebjee, MH, et al. Tissue inhibitor of metalloproteinase-1 and matrix metalloproteinase-9 levels in patients with hypertension Relationship to tissue Doppler indices of diastolic relaxation. Am J Hypertens. 2004; 17:770-4.
Tayebjee, MH, et al. Tissue inhibitor of metalloproteinse-1 is a marker of diastolic dysfunction using tissue doppler in patients with type 2 diabetes and hypertension. Eur J Clin Invest. 2005;35:8-12.
Timms, PM, et al. Plasma tissue inhibitor of metalloproteinase-1 levels are elevated in essential hypertension and related to left ventricular hypertrophy. Am J Hyper. 2002:15:269-272.
Tsuruda, T, et al. Matrix metalloproteinases: pathways of induction by bioactive molecules. Heart Fail Rev. 2004;9:53-61.
U.S. Appl. No. 12/307,985.
U.S. Appl. No. 12/522,238.
Voller, A. et al., Enzyme immunoassays with special reference to ELISA techniques. J. Clin. Pathol. 31:507-520 (1978).
Vu, TH and Werb Z. Matrix metalloproteinases: effectors of development and normal physiology. Genes Dev 2000;14:2123-2133.
Wachtell, K, et al. Left ventricular filling patterns in patients with systemic hypertension and left ventricular hypertrophy (The Life Study). Am J Cardiol. 2000;85:466-472.
Wassef, M, et al. Pathogenesis of abdominal aortic aneurysms: a multidisciplinary research program supported by the National Heart, Lung, and Blood Institute. J Vas Surg 2001; 34: 730-8.
Weber, KT and Brilla, CG. Pathological hypertrophy and cardiac interstitium. Fibrosis and renin-angiotensin-aldosterone system. Circulation 1991; 83: 1849-65 (Part 1).
Weber, KT and Brilla, CG. Pathological hypertrophy and cardiac interstitium. Fibrosis and renin-angiotensin-aldosterone system. Circulation 1991; 83: 1849-65 (Part 2).
Weber, KT, et al. Structural remodeling in hypertensive heart disease and the role of hormones. Hypertension. 1994;23:869-877.
Wilson, EM, et al. Plasma matrix metalloproteinase and inhibitor profiles in patients with heart failure. J Cardiac Failure. 2002;8:390-398.
Woessner, JF and Nagase, H. Activation of the zymogen forms of MMPs. In: Matrix metalloproteinases and TIMPs. Oxford University Press, Oxford UK, 2000 pp. 72-86.
Yarbrough, WM, et al. Selective targeting and timing of matrix metalloproteinase inhibition in post-myocardial infarction remodeling. Circulation. 2003;108:1753-1759.
Yasmin, et al. Matrix metalloproteinase-9 (MMP-9), MMP-2, and serum elastase activity are associated with systolic hypertension and arterial stiffness. Arterioscler Thromb Vasc Biol. 2005;25:372.
Zervoudaki, A, et al. Plasma levels of active extracellular matrix metalloproteinases 2 and 9 in patients with essential hypertension before and after antihypertensive treatment. J Hum Hypertens. 2003;17:119-124.
Zile, MR and Brutsaert DL. New concepts in diastolic dysfunction and diastolic heart failure. Part II: Causal mechanisms and treatment. Circulation. 2002;105:1503-1508.
Zile, MR and Brutsaert, DL. New concepts in diastolic dysfunction and diastolic heart failure. Part I: Diagnosis, prognosis, measurements of diastolic function. Circulation. 2002;105:1387-1393.
Martos, et al., "Diastolic Heart Failure: Evidence of Increased Myocardial Collagen Turnover Linked to Diastolic Dysfunction," *Circulation*, 115(7):888-95 (2007).
Mukherjee, et al., "Selective induction of matrix metalloproteinases and tissue inhibitor of metalloproteinases in atrial and ventricular myocardium in patients with atrial fibrillation," *American J of Cardiol.*, 97(4):532-37 (2006).
Spinale, et al., "Extracellular degradative pathways in myocardial remodeling and progression to heart failure," *J Cardiac Failure*, 8:S332-8 (2002).
Spinale, et al., "Matrix metalloproteinase inhibition during developing congestive heart failure in pigs: effects on left ventricular geometry and function," *Circ Res*, 85:364-76 (1999).
Related U.S. Appl. No. 12/944,670, filed Nov. 11, 2010.
Related U.S. Appl. No. 13/128,200, filed Sep. 22, 2011.
Related U.S. Appl. No. 13/884,861, filed May 10, 2013.
Related U.S. Appl. No. 13/884,867, filed Aug. 30, 2013.
Extended European Search Report, dated Apr. 12, 2012, in connection with related European Application No. 9825376.8.
International Search Report, dated May 23, 2012, in connection with related International Application No. PCT/US2011/060448.
International Preliminary Report on Patentability and Written Opinion, dated May 14, 2013, in connection with related International Application No. PCT/US2011/060448.
International Search Report, dated Aug. 27, 2008, in connection with corresponding International Application No. PCT/US2007/067292.
International Preliminary Report on Patentability and Written Opinion, dated Nov. 11, 2008, in connection with corresponding International Application No. PCT/US2007/067292.
International Search Report, dated Mar. 10, 2008, in connection with related International Application No. PCT/US2007/073214.
International Preliminary Report on Patentability and Written Opinion, dated Jan. 13, 2009, in connection with related International Application No. PCT/US2007/073214.

(56) References Cited

OTHER PUBLICATIONS

International Search Report, dated Sep. 23, 2008, in connection with related International Application No. PCT/US2008/000125.

International Preliminary Report on Patentability and Written Opinion, dated Jul. 7, 2009, in connection with related International Application No. PCT/US2008/000125.

International Search Report, dated Apr. 2, 2010, in connection with related International Application No. PCT/US2009/063309.

International Preliminary Report on Patentability and Written Opinion, dated May 10, 2011, in connection with related International Application No. PCT/US2009/063309.

International Search Report, dated Feb. 11, 2013, in connection with related International Application No. PCT/US2011/060422.

International Preliminary Report on Patentability and Written Opinion, dated May 14, 2013, in connection with related International Application No. PCT/US2011/060422.

Related International Application No. PCT/US2013/048280, filed Jun. 27, 2013.

* cited by examiner a: Patient with established arterial hypertension requiring treatment
b: Algorithm for assessing heart failure risk

DETECTING DIASTOLIC HEART FAILURE BY PROTEASE AND PROTEASE INHIBITOR PLASMA PROFILING

CROSS-REFERENCE TO RELATED APPLICATIONS

This application claims benefit of U.S. Provisional Application No. 60/798,953, filed May 9, 2006 and U.S. Provisional Application No. 60/893,781, filed Mar. 8, 2007, which are hereby incorporated herein by reference in their entirety.

STATEMENT REGARDING FEDERALLY SPONSORED RESEARCH

This invention was made with government support under contract number VA Merit Review (Spinale 0001) Research Service of the Department of Veterans Affairs, and under contract numbers PO1-HL-48788, RO1-HL-59165, and MO1-RR-01070-251 granted by the National Heart, Lung, and Blood Institute. The government has certain rights in the invention.

BACKGROUND

Despite significant advancements in high blood pressure (hypertension) medicines and the recognition that hypertension is a significant risk factor for the development of heart failure, this condition remains a major cardiovascular disease in the United States. One particular problem with identifying patients at risk for developing hypertensive heart failure is the lack of a rapid screening test to identify patients that have changes occurring in the heart muscle itself secondary to hypertension. With prolonged hypertension, the muscle mass and size of the heart increases, but this may not occur until later in the disease process. One unique and critical event in the progression to hypertensive heart disease and heart failure is that increased fibrosis occurs within the heart muscle itself. The molecular basis for this change remains unknown.

BRIEF SUMMARY

In accordance with the purpose of this invention, as embodied and broadly described herein, this invention relates to unique patterns of MMPs/TIMPs that occur in patients with developing hypertensive heart failure that were actually predictive of the presence of abnormal heart function—heretofore only possible to identify with expensive and difficult to apply tests. The unique pattern of MMPs/TIMPs are used in methods for the identification of patients at risk of and soon to develop heart failure secondary to hypertension.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 9 shows alogorithm for using MMP and TIMP levels to determine treatment of patients with hypertension.

DETAILED DESCRIPTION

Figure 1:
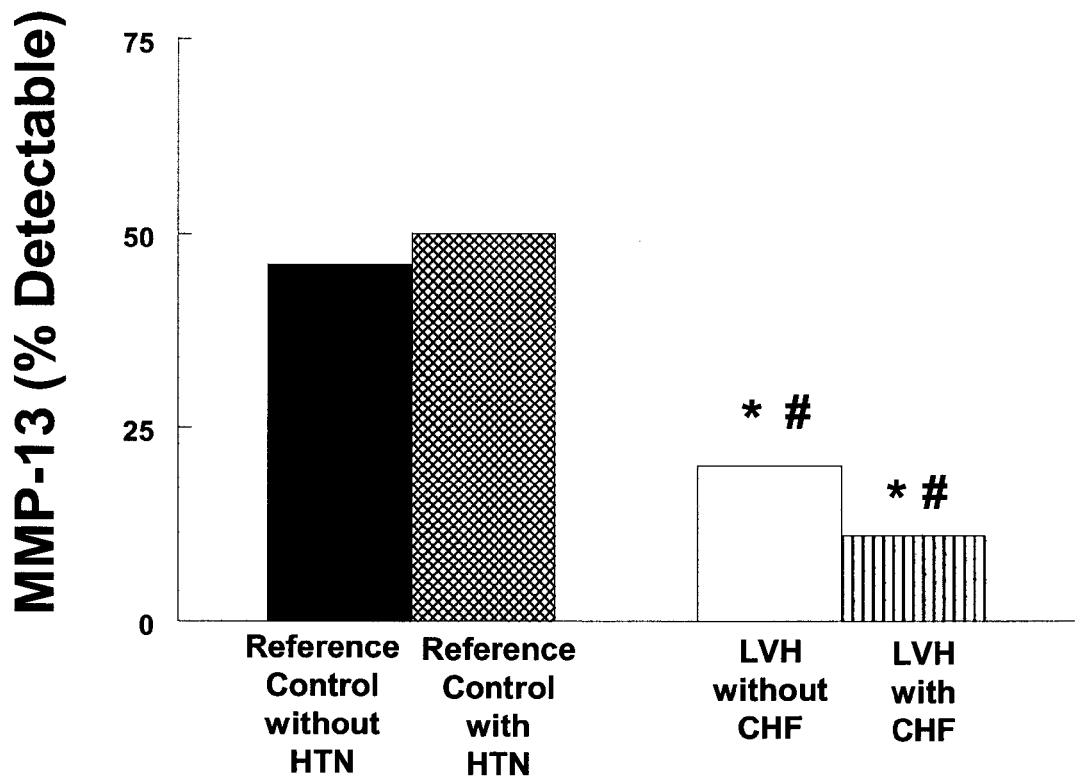
FIG. 1 shows MMP-13 detectability in reference control with and without hypertension and in LVH with and without chronic heart failure. MMP-13 detectability decreased significantly in LVH patients. *=$p<0.05$ vs Reference control without Hypertension, #=$p<0.05$ vs Reference control with Hypertension, Δ=$p<0.05$ vs LVH without CHF.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification. More specifically, the MMPs and TIMPs whose amounts are measured can have those measurements taken in any order.

A. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

"Subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject may to an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As defined herein "sample" refers to any sample obtained from an organism. Examples of biological samples include body fluids and tissue specimens. The source of the sample may be physiological media as blood, serum, plasma, breast milk, pus, tissue scrapings, washings, urine, tissue, such as lymph nodes or the like.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Methods

1. Heart Failure

Congestive heart failure (CHF), also called congestive cardiac failure (CCF) or just heart failure, is a condition that can result from any structural or functional cardiac disorder that impairs the ability of the heart to fill with or pump a sufficient amount of blood throughout the body. Thus, the disclosed method can be used to treat any form of heart failure.

Because not all patients have volume overload at the time of initial or subsequent evaluation, the term "heart failure" is preferred over the older term "congestive heart failure". Causes and contributing factors to congestive heart failure include the following (with specific reference to left (L) or right (R) sides): Genetic family history of CHF, Ischemic heart disease/Myocardial infarction (coronary artery disease), Infection, Alcohol ingestion, Heartworms, Anemia, Thyrotoxicosis (hyperthyroidism), Arrhythmia, Hypertension (L), Coarctation of the aorta (L), Aortic stenosis/regurgitation (L), Mitral regurgitation (L), Pulmonary stenosis/Pulmonary hypertension/Pulmonary embolism all leading to cor pulmonale (R), and Mitral valve disease (L).

There are many different ways to categorize heart failure, including: the side of the heart involved, (left heart failure versus right heart failure), whether the abnormality is due to contraction or relaxation of the heart (systolic heart failure vs. diastolic heart failure), and whether the abnormality is due to low cardiac output or low systemic vascular resistance (low-output heart failure vs. high-output heart failure).

Congestive heart failure (CHF) is a constellation of signs and symptoms (i.e. shortness of breath, fluid accumulation) due to an underlying disorder in cardiac performance-notably left ventricular (LV) function. The causes of CHF can be diverse, but fall into 3 main categories: following a heart attack (myocardial infarction), with hypertensive heart disease, and with intrinsic muscle disease generically called cardiomyopathy. It has been difficult to identify the underlying causes of CHF such as that caused by hypertensive heart disease, and this is focus of the present methods. Specifically, hypertensive heart disease causes growth of the LV muscle—called hypertrophy. LV hypertrophy (LVH) in and of itself can cause defects in cardiac performance, but a blood test to identify LVH quickly and accurately has not been available previously. This application identifies a new and validated approach to identify patients with LVH. If the LVH process continues, or is not adequately treated, then patients will develop signs and symptoms of CHF primarily due to diastolic heart failure (DHF). However it has been difficult up to the present time to identify patients that suffer from CHF that primarily have DHF, and it has not been possible to identify these patients with a simple and rapid blood test. This application identifies a new and validated approach to identify patients that not only have the presence of LVH, but also those that will be at risk for the development of DHF, and identification of those that have DHF. Thus, this invention provides a means to detect the presence of LVH, predict those patients that will be at high risk for development of DHF, and to identify those patients with DHF. Through the use of a small sample of bodily fluid, and for the example identified below, a blood sample, it will be possible to perform, 4 independent, but not necessarily exclusive, applications of this method: screening, prediction/prognosis, diagnosis, and treatment monitoring.

Thus, disclosed is a method to diagnose a subject with left ventricular hypertrophy (LVH, HCM or HOCM). For example, provided is a method of detecting LVH in a subject, comprising identifying a profile of matrix metalloproteinases (MMPs) and tissue inhibitors of matrix metalloproteinases (TIMPs) from a body fluid of the subject that is associated herein with the existence of diastolic heart failure (DHF). Also provided is a method of predicting diastolic heart failure in a subject, comprising identifying a profile of matrix metalloproteinases (MMPs) and tissue inhibitors of matrix metalloproteinases (TIMPs) from a body fluid of the subject that is associated herein with the likely development of diastolic heart failure (DHF).

2. MMPs

Matrix metalloproteinases (MMPs) are zinc-dependent endopeptidases; other family members are adamalysins, serralysins, and astacins. The MMPs belong to a larger family of proteases known as the metzincin superfamily.

The MMPs share a common domain structure. The three common domains are the pro-peptide, the catalytic domain and the haemopexin-like C-terminal domain which is linked to the catalytic domain by a flexible hinge region.

The MMPs are initially synthesised as inactive zymogens with a pro-peptide domain that must be removed before the enzyme is active. The pro-peptide domain is part of "cysteine switch" this contains a conserved cysteine residue which interacts with the zinc in the active site and prevents binding and cleavage of the substrate keeping the enzyme in an inactive form. In the majority of the MMPs the cysteine residue is in the conserved sequence PRCGxPD. Some MMPs have a prohormone convertase cleavage site (Furin-like) as part of this domain which when cleaved activates the enzyme. MMP-23A and MMP-23B include a transmembrane segment in this domain (PMID 10945999).

X-ray crystallographic structures of several MMP catalytic domains have shown that this domain is an oblate sphere measuring 35×30×30 Å (3.5×3×3 nm). The active site is a 20 Å (2 nm) groove that runs across the catalytic domain. In the part of the catalytic domain forming the active site there is a catalytically important Zn2+ ion, which is bound by three histidine residues found in the conserved sequence HExxHxxGxxH. Hence, this sequence is a zinc-binding motif.

The gelatinases, such as MMP-2, incorporate Fibronectin type II modules inserted immediately before in the zinc-binding motif in the catalytic domain (PMID 12486137).

The catalytic domain is connected to the C-terminal domain by a flexible hinge or linker region. This is up to 75 amino acids long, and has no determinable structure.

The C-terminal domain has structural similarities to the serum protein haemopexin. It has a four bladed β-propeller structure. β-propeller structures provide a large flat surface which is thought to be involved in protein-protein interactions. This determines substrate specificity and is the site for interaction with TIMP's. The haemopexin-like domain is absent in MMP-7, MMP-23, MMP-26 and the plant and nematode. MT-MMPs are anchored to the plasma membrane, through this domain and some of these have cytoplasmic domains.

The MMPs can be subdivided in different ways. Use of bioinformatic methods to compare the primary sequences of the MMPs suggest the following evolutionary groupings of the MMPs: MMP-19; MMPs 11, 14, 15, 16 and 17; MMP-2 and MMP-9; all the other MMPs.

Analysis of the catalytic domains in isolation suggests that the catalytic domains evolved further once the major groups had differentiated, as is also indicated by the substrate specificities of the enzymes. The most commonly used groupings (by researchers in MMP biology) are based partly on historical assessment of the substrate specificity of the MMP and partly on the cellular localisation of the MMP. These groups are the collagenases, the gelatinases, the stromelysins, and the membrane type MMPs (MT-MMPs). It is becoming increasingly clear that these divisions are somewhat artificial as there are a number of MMPs that do not fit into any of the traditional groups.

The collagenases are capable of degrading triple-helical fibrillar collagens into distinctive ¾ and ¼ fragments. These collagens are the major components of bone and cartilage, and MMPs are the only known mammalian enzymes capable of degrading them. Traditionally, the collagenases are: MMP-1 (Interstitial collagenase), MMP-8 (Neutrophil collagenase), MMP-13 (Collagenase 3), MMP-18 (Collagenase 4, xcol4, xenopus collagenase. No known human orthologue), MMP-14 (MT1-MMP) has also been shown to cleave fibrillar collagen, and more controversially there is evidence that MMP-2 is capable of collagenolysis.

The stromelysins display a broad ability to cleave extracellular matrix proteins but are unable to cleave the triple-helical fibrillar collagens. The three canonical members of this group are: MMP-3 (Stromelysin 1), MMP-10 (Stromelysin 2), and MMP-11 (Stromelysin 3). MMP-11 shows more similarity to the MT-MMPs, is convertase-activatable and is secreted therefore usually associated to convertase-activatable MMPs.

The matrilysins include MMP-7 (Matrilysin, PUMP) and MMP-26 (Matrilysin-2, endometase).

The main substrates of gelatinasese are type IV collagen and gelatin, and these enzymes are distinguished by the presence of an additional domain inserted into the catalytic domain. This gelatin-binding region is positioned immediately before the zinc binding motif, and forms a separate folding unit which does not disrupt the structure of the catalytic domain. The two members of this sub-group are: MMP-2 (72 kDa gelatinase, gelatinase-A) and MMP-9 (92 kDa gelatinase, gelatinase-B).

The secreted MMPs include MMP-11 (Stromelysin 3), MMP-21 (X-MMP), and MMP-28 (Epilysin).

The membrane-bound MMPs include: the type-II transmembrane cysteine array MMP-23, the glycosyl phosphatidylinositol-attached MMPs 17 and 25 (MT4-MMP and MT6-MMP respectively), and the type-I transmembrane MMPs 14, 15, 16, 24 (MT1-MMP, MT2-MMP, MT3-MMP, and MT5-MMP respectively).

All 6 MT-MMPs have a furin cleavage site in the propeptide, which is a feature also shared by MMP-11.

Other MMPs include MMP-12 (Macrophage metalloelastase), MMP-19 (RASI-1, occasionally referred to as stromelysin-4), Enamelysin (MMP-20), and MMP-27 (MMP-22, C-MMP), MMP-23A (CA-MMP), and MMP-23B.

3. TIMPs

The MMPs are inhibited by specific endogenous tissue inhibitor of metalloproteinases (TIMPs), which comprise a family of four protease inhibitors: TIMP-1, TIMP-2, TIMP-3 and TIMP-4. Overall, all MMPs are inhibited by TIMPs once they are activated but the gelatinases (MMP-2 and MMP-9) can form complexes with TIMPs when the enzymes are in the latent form. The complex of latent MMP-2 (pro-MMP-2) with TIMP-2 serves to facilitate the activation of pro-MMP-2 at the cell surface by MT1-MMP (MMP-14), a membrane-anchored MMP.

4. MMP/TIMP Ratio

One of the unique characteristics for MMP-TIMP profiling in hypertensive heart disease is to utilize the cardiac specific TIMP, TIMP-4, and place this in context with an MMP which changes in greater magnitude in myocardial infarction and hypertensive patients. Also disclosed are ratios of an MMP, such as MMP-9 or MMP-13, to a TIMP, such as TIMP-1, TIMP-2, or TIMP-4. These ratios are used for the first time herein as diagnostic differentials and for identifying patients with distinctly different disease states.

5. Plasma Screening

A key advantage of the present teaching is that the herein disclosed methods afford a more rapid and simplified process to identify from a tissue or bodily fluid a subject at risk for developing adverse LVH as well as identify patients in which this process is occurring at an accelerated pace. Thus, the herein disclosed methods can comprise the detection of MMPs and TIMPs in bodily fluid of the subject, such as blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

Blood plasma is the liquid component of blood, in which the blood cells are suspended. Plasma is the largest single component of blood, making up about 55% of total blood volume. Serum refers to blood plasma in which clotting factors (such as fibrin) have been removed. Blood plasma contains many vital proteins including fibrinogen, globulins and human serum albumin. Sometimes blood plasma can contain viral impurities which must be extracted through viral processing.

6. Immunoassay

There are numerous methods for detecting analytes, such as proteins, such as MMPs and TIMPs, known or newly discovered in the art, which can be used in the disclosed methods. For example, MMPs and TIMPs can be detected using standard immunodetection methods. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-I $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.18; Cy3.5™; Cy3™; Cy5.18; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Dil (DilC18(3)); 1Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP(S65T); GFP red shifted (rs-GFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/

Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-lndo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (PI); PYMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl)quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250: 4007-4021 (1975), herein incorporated by reference in its entirety for its teaching regarding two-dimensional electrophoresis methods. Other examples include but are not limited to, those found in Anderson, L and Anderson, NG, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121: 321349 (1964), each of which is herein incorporated by reference in its entirety for teachings regarding electrophoresis methods.

Laemmli, U.K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., Protein Methods (2d edition 1996) and E. Harlow & D. Lane, Antibodies, a Laboratory Manual (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis-I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}$P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, available at <http://www.promega.com/faq/gelshfaq.html> (last visited Mar. 25, 2005), which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}$I or $^{131}$I are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995;U.S. Pat. No. 4,376,110, each of which is incorporated herein by reference in its entirety and specifically for teachings regarding ELISA methods.

Variations of ELISA techniques are know to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled third binding agent.

"Under conditions effective to allow immunecomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, the occurrence of even minute amounts of immunecomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialised chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include colour coding for microbeads (Luminex, Austin, Tex.; Bio-Rad Laboratories) and semiconductor nanocrystals (e.g., QDOts™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, Wash.) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a polylysine backbone immobilised on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; Bioinvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, Mass.) and 'Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colours. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumour extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale 'proteome chips' promise to be very useful in identification of functional interactions, drug screening, etc. (Proteometrix, Branford, Conn.).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

The MMP/TIMP profiles disclosed herein are based on measurements of individual MMPs or TIMPs. The amounts of these can be measured by any means known to provide an acceptable indication of how much of any of these is present in the sample being analyzed. An example of a means of measuring is provided in the Examples. The process of measuring an amount of an analyte (e.g., MPP or TIMP) includes measurement of no amount or an undetectable amount of the analyte.

Figure 8:
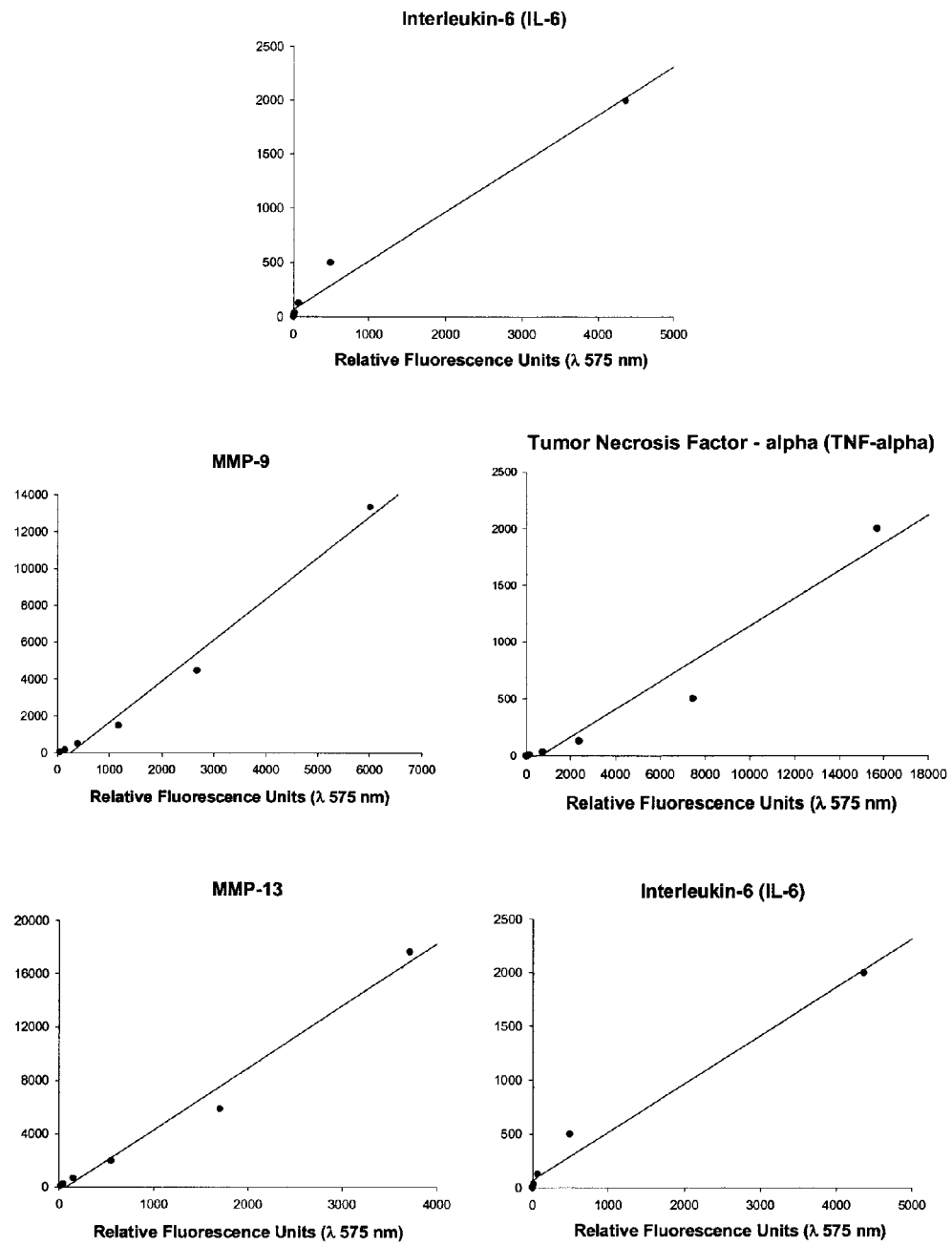
FIG. 8 shows calibration curves for MMP-9, MMP-13, TNF-α, and IL-6 as determined by multiplex analysis.

The techniques and approaches for measuring MMP and TIMPs which formed the basis of this invention were based upon high sensitivity immunoassays. Several of these immunoassays were developed by this laboratory (i.e. TIMP-4 assay measurements). The immunoassay approach which was standardized for providing the measurements shown in Table 4 was performed by an enzyme linked immuno-assay (ELISA). However, other more sensitive and rapid methods for measuring blood levels of MMPs and TIMPs have been performed by this laboratory and these include the use of a multiplex assay system. In this example, multiple analytes in volume-limited samples, such as plasma or other biological samples, can be measured using a bead-based multiplex sandwich immunoassay. This emergent technique for multiplex analysis is built on technology that combines the sensitivity of ELISA with flow cytometric detection, allowing for the specific measurement of up to 100 different analytes within a single sample of less than 50 µl. This approach allows for the measurement of multiple MMPs and TIMPs in a small blood sample. This type of approach is well-suited for the diagnostic, prognostic, predictive and therapeutic monitoring applications that are described herein. Specifically, to measure analyte concentrations simultaneously, the microbeads are incubated with sample (i.e. blood sample) and allowed to form complexes with the specific analytes of interest (i.e. MMPs). Detection antibodies (biotinylated), specific for a second epitope on each analyte, are then added to the mixture and allowed to bind to the microbeads complexed with analyte. The mixture is then incubated with a fluorescent reporter molecule (streptavidin-phycoerythrin) and the entire sample is passed through a two-laser flow cytometric detector. One laser detects the precise fluorescence of the microbead which defines the specific analyte being examined, and the other laser detects the amount of reporter fluorescence which is directly proportional to the amount of analyte bound. This process has been applied to a number of MMPs and other analytes that hold potential bearing to the CHF process and these are shown in FIG. 8 and Table 1. This is but one example of how single or multiple analytes can be measured with a very small blood sample. Other examples of measurements that have been performed with respect to MMP/TIMP analytes include radioimmunoassay and immunoblotting assays. These approaches are also antibody based.

TABLE 1

Concentration range of analytes used for calibration and linear regression statistics for calculated standard curves.

| Analyte | Range (pg/ml) | $R^2$ | P-value |
|---|---|---|---|
| MMP-1 | 14.1-3433.33 | 0.96 | 0.0004 |
| MMP-2 | 75.5-18333.33 | 0.99 | 0.0001 |

TABLE 1-continued

Concentration range of analytes used for calibration and linear regression statistics for calculated standard curves.

| Analyte | Range (pg/ml) | $R^2$ | P-value |
|---|---|---|---|
| MMP-3 | 13.0-3166.67 | 0.97 | 0.0002 |
| MMP-7 | 96.0-23333.33 | 0.98 | 0.0001 |
| MMP-8 | 83.7-20333.33 | 0.96 | 0.0004 |
| MMP-9 | 54.9-13333.33 | 0.98 | 0.0001 |
| MMP-12 | 12.8-31000.00 | 0.97 | 0.0003 |
| MMP-13 | 72.7-17666.70 | 0.98 | 0.0001 |
| TNF-alpha | 1.95-2000.0 | 0.95 | 0.0002 |
| IL-1 beta | 1.95-2000.0 | 0.94 | 0.0002 |
| IL-2 | 1.95-2000.0 | 0.98 | 0.0001 |
| IL-6 | 1.95-2000.0 | 0.98 | 0.0001 |
| IL-8 | 1.95-2000.0 | 0.91 | 0.0007 |
| IL-10 | 1.95-2000.0 | 0.97 | 0.0001 |
| G-CSF | 1.95-2000.0 | 0.99 | 0.0001 |
| INF-gamma | 1.95-2000.0 | 0.99 | 0.0001 |
| MCP-1 | 1.95-2000.0 | 0.96 | 0.0001 |
| MIP-beta | 1.95-2000.0 | 0.91 | 0.0008 |

7. Antibodies

Antibodies specific for MMPs and TIMPs are known and commercially available. Examples of antibodies are provided in Table 2.

TABLE 2

MMP/TIMP Antibodies

| Analyte | Catalog # | Vendor |
|---|---|---|
| MMP-1 | IM52 | Oncogene |
|  | PC311 | Oncogene |
|  | IM35L | Oncogene |
|  | AB806 | Chemicon |
| MMP-2 | AB19015 | Chemicon |
|  | PC342 | Oncogene |
|  | IM33L | Oncogene |
|  | MAB3308 | Chemicon |
|  | AB19015 | Chemicon |
|  | MAB13405 | Chemicon |
|  | AB809 | Chemicon |
| MMP-3 | PC310 | Oncogene |
|  | AB810 | Chemicon |
|  | AB811 | Chemicon |
|  | IM36L | Oncogene |
| MMP-7 | PC492 | Oncogene |
|  | AB8118 | Chemicon |
|  | AB8117 | Chemicon |
| MMP-8 | 3528-100 | BioVision |
|  | PC493 | Oncogene |
|  | IM38L | Oncogene |
| MMP-9 | AB19047 | Chemicon |
|  | IM09 | Oncogene |
|  | PC309 | Oncogene |
|  | AB804 | Chemicon |
| MMP-11 | PC467 | Oncogene |
| MMP-12 | AB19051 | Chemicon |
|  | RPI-MMP-12 | TriplePointBiologics |
|  | PC494 | Oncogene |
| MMP-13 | AB8114 | Chemicon |
|  | PC542 | Oncogene |
|  | 3533-100 | BioVision |
|  | AB19055 | Chemicon |
| MMP-14 | AB815 | Chemicon |
|  | AB8102 | Chemicon |
|  | RDI-MMP14 | Res. Diagnostics, Inc. |
|  | MAB3317 | Chemicon |
|  | AB8221 | Chemicon |
|  | AB8103 | Chemicon |
| MMP-15 | AB850 | Chemicon |
|  | MAB3320 | Chemicon |
|  | AB855 | Chemicon |
| TIMP-1 | OPA1-08512 | ABR |
|  | AB8122 | Chemicon |

TABLE 2-continued

MMP/TIMP Antibodies

| Analyte | Catalog # | Vendor |
|---------|-----------|--------|
|         | AB770     | Chemicon |
|         | AB8116    | Chemicon |
|         | PC500     | Oncogene |
| TIMP-2  | AB801     | Chemicon |
|         | RP2T2     | Triple Point Biologics |
|         | IM11L     | Oncogene |
|         | CL1T2     | CedarLane |
|         | MAB3310   | Chemicon |
|         | AB8107    | Chemicon |
| TIMP-3  | CL2T3     | CedarLane |
|         | IM43L     | Oncogene |
|         | H-TIMP-3  | Triple Point Biologics |
| TIMP-4  | AB816     | Chemicon |
|         | MAB974    | R&D Systems |
|         | Ab19087   | Chemicon |

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with MMPs or TIMPs. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA*, 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

8. Reference Values

Provided are profiles of MMPs and/or TIMPs that are indicative of the existence of DHF or are predictive of the development of DHF in a subject. The profiles that are indicative of the existence of DHF or are predictive of the development of DHF in a subject can be relative to a normal value. A normal value for a given analyte (MMP or TIMP) can be a reference value for an age matched subject that is confirmed to have no evidence of significant cardiovascular disease. Thus, the normal value can be a population-based value derived from a significant number of healthy individuals. These reference normal values can be obtained from population based studies. There are large population based studies for example that have identified relative levels of TIMP-1 (Framingham Heart Study, Circulation 2004; 109:2850-2856) in a reference group to approximately 800 ng/mL which is consistent with the reference control values disclosed herein.

Alternatively, the normal value can be a value that is considered normal for a given subject. For example, baseline measurements of the relevant analytes can be made for a healthy individual, and used for comparison against later-acquired measurements from that individual to identify current disease or progression toward hypertensive heart disease.

A discrete observation, e.g., for MMP-13, is where a continuous variable such as a plasma concentration of a given analyte is converted to a dichotomous variable. In this particular instance a +/− value would be assigned to MMP-13 where a value of greater than 10 ng/mL would be considered a detectable, or positive value and a value less than 10 ng/mL to be a negative value.

For example, provided is a method of diagnosing the absence of LVH associated with hypertensive heart disease in a subject comprising measuring MMP and/or TIMP levels in a tissue or bodily fluid of the subject and comparing said levels to reference values. Thus, normal values for MMP-2, MMP-9, MMP-7, MMP-13, MMP-8, TIMP-1, TIMP-2, and/or TIMP-4 is an indication of the absence of left ventricular hypertophy associated with hypertensive heart disease.

In some aspects, MMP-2 plasma levels within normal range is an indication of the absence of LVH associated with hypertensive heart disease. In some aspects, MMP-9 plasma levels within normal range is an indication of the absence of LVH associated with hypertensive heart disease. In some aspects, MMP-13 plasma levels within normal range is an indication of the absence of LVH associated with hypertensive heart disease. In some aspects, TIMP-1 plasma levels within normal range is an indication of the absence of LVH associated with hypertensive heart disease. In some aspects, TIMP-2 plasma levels within normal range is an indication of the absence of LVH associated with hypertensive heart disease. In some aspects, TIMP-4 plasma levels within normal range is an indication of the absence of LVH associated with hypertensive heart disease.

In some aspects, MMP-2 plasma levels greater than about 1000 ng/ml, including greater than about 1000, 1100, 1200, 1300, 1400, and 1500 ng/ml, is an indication of the absence of LVH associated with hypertensive heart disease.

In some aspects, MMP-9 plasma levels less than about 20 ng/ml, including less than about 20, 19, 18, 17, 16, 15, 14, 13, 12, 11, 10, 9, 8, 7, 6, 5, 4, 3, 2, or 1 ng/ml, is an indication of the absence of LVH associated with hypertensive heart disease.

In some aspects, detactable MMP-13 plasma levels greater than about 5 ng/ml, including less than about 5, 6, 7, 8, 9, 10, 11, 12, 13, 14, 15, 20 ng/ml, is an indication of the absence of LVH associated with hypertensive heart disease.

In some aspects, TIMP-1 plasma levels less than about 1000 ng/ml, including greater than about 1000, 900, 800, 700, 600, 500, 400, 300, 200, 100, 50, 40, 30, 20, or 10 ng/ml, is an indication of the absence of LVH associated with hypertensive heart disease.

In some aspects, TIMP-2 plasma levels less than about 50 ng/ml, including greater than about 50, 49, 48, 47, 46, 45, 44, 43, 42, 41, 40, 35, 30, 25, 20, 15, or 10 ng/ml, is an indication of the absence of LVH associated with hypertensive heart disease.

In some aspects, TIMP-4 plasma levels less than about 2 ng/ml, including greater than about 2.0, 1.9, 1.8, 1.7, 1.6, 1.5, 1.4, 1.3, 1.2, 1.1, 1.0, 0.5, or 0.1 ng/ml, is an indication of the absence of LVH associated with hypertensive heart disease.

The method can further comprise measuring plasma levels of two or more MMPs and/or TIMPs. For example, the method can comprise measuring two, three, four, five, six, seven, or eight of MMP-2, MMP-9, MMP-7, MMP-13, MMP-8, TIMP-1, TIMP-2, and TIMP-4. Thus, the method can comprise measuring MMP-2 and MMP-9, or MMP-2 and MMP-7, MMP-2 and MMP-13, MMP-2 and MMP-8, MMP-2 and TIMP-1, MMP-2 and TIMP-2, MMP-2 and TIMP-4, MMP-9 and MMP-7, MMP-9 and MMP-13, MMP-9 and MMP-8, MMP-9 and TIMP-1, MMP-9 and TIMP-2, MMP-9 and TIMP-4, MMP-7 and MMP-13, MMP-7 and MMP-8, MMP-7 and TIMP-1, MMP-7 and TIMP-2, MMP-7 and TIMP-4, MMP-13 and MMP-8, MMP-13 and TIMP-1, MMP-13 and TIMP-13, MMP-13 and TIMP-4, MMP-8 and TIMP-1, MMP-8 and TIMP-2, MMP-8 and TIMP-4, TIMP-1 and TIMP-2, TIMP-1 and TIMP-4, TIMP-2 and TIMP-4. Thus, the method can comprise measuring MMP-2, MMP-13 and TIMP-1; MMP-2, MMP-13 and TIMP-2; MMP-2, MMP-13 and TIMP-4; MMP-13, TIMP-1, and TIMP-2; MMP-13, TIMP-1, and TIMP-4; MMP-13, TIMP-2, and TIMP-4. Thus, the method can comprise measuring MMP-2, MMP-13, TIMP-1, and TIMP-2; MMP-2, MMP-13, TIMP-1, and TIMP-4; MMP-2, MMP-13, TIMP-2, and TIMP-4; MMP-13, TIMP-1, TIMP-2, and TIMP-4; MMP-2, TIMP-1, TIMP-2, and TIMP-4. Thus, the method can comprise measuring MMP-2, MMP-13, TIMP-1, TIMP-2, and TIMP-4. Other combinations of these analytes are contemplated and disclosed herein.

The method can further comprise calculating the ratio of one or more of the MMPs or TIMPs to other MMPs or TIMPs. For example, the method can comprise calculating the ratio of MMP-9 to TIMP-1, TIMP-2 or TIMP-4.

For example, in some aspects, a ratio of MMP-9/TIMP-1 plasma levels greater than about $7 \times 10^3$, including greater than about $7 \times 10^3$, $8 \times 10^3$, $9 \times 10^3$, $10 \times 10^3$, $11 \times 10^3$, $12 \times 10^3$, $13 \times 10^3$ or $14 \times 10^3$, is an indication of the absence of LVH associated with hypertensive heart disease.

In some aspects, a ratio of MMP-9/TIMP-2 plasma levels greater than about $10 \times 10^4$, including greater than about $10 \times 10^4$, $20 \times 10^4$, $30 \times 10^4$, or $40 \times 10^4$, is an indication of the absence of LVH associated with hypertensive heart disease.

In some aspects, a ratio of MMP-9/TIMP-4 plasma levels greater than about 1, including greater than about 1, 2, 3, 4, 5, 6, 7, 8, or 9, is an indication of the absence of LVH associated with hypertensive heart disease.

The reference normal values and those measured at screening in hypertensive patients is shown in Table 3. In this instance, MMP-2 values may be reduced in hypertensive patients with LVH with no change in MMP-7 values. However, a discrete observation for MMP-13 will occur in that this will not be detected in hypertensive patients with LVH. Therefore a cutpoint of below 10 ng/mL would be considered a diagnostic criteria for hypertension and heart failure. TIMP-1 and TIMP-4 levels will be 50% higher in hypertensive patients with LVH compared to reference control values. The MMP-9/TIMP-4 ratio will be reduced by over 50% in hypertensive patients with LVH when compared to reference normal values.

TABLE 3

MMP and TIMP Data; Reference Normal Values and Hypertensive Heart Disease; Diagnostic Percent Cutpoints

| | Normal | Hypertension and Failure | % change |
|---|---|---|---|
| MMP-2 (ng/mL) | 1387 ± 39 | 1205 ± 44* | ▼ 20% or greater |
| MMP-7 (ng/mL) | 2.5 ± 0.2 | similar to normal | NC |
| MMP-13 (ng/mL) | Detectable | Non-Detectable (<10) | Discrete value |
| MMP-9 (ng/mL) | 13 ± 3 | 26 ± 3* | ▲ 50% or greater |
| TIMP-1 (ng/mL) | 997 ± 36 | 1291 ± 70* | ▲ 50% or greater |
| TIMP-2 (ng/mL) | 44 ± 4 | 58 ± 7 | NC |
| TIMP-4 (ng/mL) | 1.9 ± 0.1 | 3.8 ± 0.1 | ▲ 50% or greater |
| MMP-9/TIMP-1 ($\times 10^{-3}$) | 14 ± 3 | 15 ± 5 | NC |

TABLE 3-continued

MMP and TIMP Data; Reference Normal Values and Hypertensive
Heart Disease; Diagnostic Percent Cutpoints

|  | Normal | Hypertension and Failure | % change |
|---|---|---|---|
| MMP-9/TIMP-2 ($\times 10^{-3}$) | 388 ± 88 | 350 ± 250 | NC |
| MMP-9/TIMP-4 | 7.8 ± 1.6 | 2.52 ± 0.4* | ▼ 50% or greater |

NC = no change from Normal
*p < 0.05 vs. Normal

9. Rapid Screening for LVH

Provided is a rapid yes/no result that can be obtained by testing levels for one particular MMP, MMP-13. A set point, which may be adjusted based upon population statistics as well as age adjusted, would be used as the effective read-out. As an example, an MMP-13 level below a threshold setting of 1, 2, 3, 4, 5, 6, 7, 8, 9, or 10 ng/mL, would justify a more intensive plasma screening portfolio and additional cardiovascular imaging studies. In other words, this rapid screening test could be applied to any large population, which would then identify those subjects that would warrant more careful testing and follow-up. There are currently no available rapid screening tests to identify patients with LVH.

Provided is a method of predicting diastolic heart failure in a subject, comprising measuring the amount of MMP-13 in a body fluid from the subject, an amount of less than 1, 2, 3, 4, 5, 6, 7, 8, 9, or 10 ng/mL or undetectable indicating the presence of LVH and being predictive of DHF. When combined with abnormal measurements of other relevant analytes disclosed herein, this measurement can detect DHF.

Plasma profiling at a primary care or medical screening encounter can be performed. This screening measurement can be made for one or more of the MMPs and/or TIMPS. If the one or more measurements falls outside reference values, additional measurements can be performed. For example, MMP-13 can be used for an initial screening such that if MMP-13 is non-detectable, then a second assay can be performed on the plasma sample. Likewise, MMP-9 and TIMP-1, TIMP-2, and/or TIMP-4 can be used for an initial screening such that if the ratio of MMP-9 to TIMP-1, TIMP-2, or TIMP-4 is less than normal limits using an established threshold, then a second assay can be performed on the plasma sample. This second test can be for the full profile shown in Table 3 or a subset thereof. If this profile meets the criteria for hypertensive heart disease, then the patient can be evaluated by more aggressive tests which could include echocardiography, catheterization, nuclear imaging as appropriate. The patient can also be evaluated for more aggressive medical management.

10. Diagnosis

Also provided is a diagnostic method that can be used, for example, with a subject that presents with signs and symptoms of CHF, but the underlying cause for this presentation is difficult to determine. This occurs quite frequently; where a patient has CHF, but whether LVH and DHF exists, and is contributory for the exacerbation of the CHF process, cannot be easily determined. The use of a simple and rapid blood test to "rule in" or "rule out" the presence of LVH and DHF, as described in this application, would provide this needed diagnostic approach. Specifically, a blood sample would be measured for MMP-13, MMP-9, MMP-2, TIMP-1, and/or TIMP-4. The obtained values would be compared to the normal reference values disclosed herein. If the values differ from the normal limits by the thresholds identified herein, then a patient can be identified to have DHF.

For example, provided is a method of diagnosing LVH in a subject comprising measuring MMP and/or TIMP levels in a tissue or bodily fluid of the subject and comparing said levels to reference values.

In some aspects, MMP-2 plasma levels less than the normal value is an indication of hypertensive heart disease. For example, an amount of MMP-2 at least about 20% less than the normal mean value can be an indication of hypertensive heart disease. In some aspects, MMP-2 plasma levels less than about 1000 ng/ml, including less than about 1000, 990, 980, 970, 960, 950, 940, 930, 920, 920, 900, 890, 880, 870, 860, 850, 840, 830, 820, 810, 800, 790, 780, 770, 760, 750, 740, 730, 720, 710, 700, 650, 600, 550, 500, 450, 400, 350, 300, 250, 200, 250, or 100 ng/ml, is an indication of hypertensive heart disease.

In some aspects, MMP-9 plasma levels greater than the normal value is an indication of hypertensive heart disease. For example, an amount of MMP-9 at least about 50% greater than the normal mean value can be an indication of hypertensive heart disease. In some aspects, MMP-9 plasma levels greater than about 20 ng/ml, including greater than about 20, 21, 22, 23, 24, 15, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 ng/ml, is an indication of hypertensive heart disease.

In some aspects, undetectable MMP-13 plasma levels is an indication of LVH. In some aspects, MMP-13 plasma levels less than about 10 ng/ml, including less than about 10, 9, 8, 7, 6, 5, 4, 3, 2, or 1 ng/ml, is an indication of LVH.

In some aspects, TIMP-1 plasma levels greater than the normal value is an indication of hypertensive heart disease. For example, an amount of TIMP-1 at least about 50% greater than the normal mean value can be an indication of LVH. In some aspects, TIMP-1 plasma levels greater than about 1000 ng/ml, including greater than about 1000, 1010, 1020, 1030, 1040, 1050, 1060, 1070, 1080, 1090, 1100, 1150, 1200, 1250, 1300, 1350, 1400, or 1500 ng/ml, is an indication of LVH.

In some aspects, TIMP-2 plasma levels greater than the normal value is an indication of LVH. For example, an amount of TIMP-2 at least about 50% greater than the normal mean value can be an indication of LVH. In some aspects, TIMP-2 plasma levels greater than about 50 ng/ml, including greater than about 50, 55, 60, 65, 70, 75, 80, 85, 90, 95, or 100 ng/ml, is an indication of LVH.

In some aspects, TIMP-4 plasma levels greater than the normal value is an indication of LVH. For example, an amount of TIMP-4 at least about 50% greater than the normal mean value can be an indication of LVH. In some aspects, TIMP-4 plasma levels greater than about 2 ng/ml, including greater than about 2, 3, 4, 5, 6, 7, 8, 9, or 10 ng/ml, is an indication of LVH.

In some aspects, MMP-7 plasma levels within normal range is an indication of LVH. In some aspects, MMP-8 plasma levels within normal range is an indication of LVH.

The method can further comprise measuring plasma levels of two or more MMPs and/or TIMPs. For example, the method can comprise measuring two, three, four, five, six, seven, or eight of MMP-2, MMP-9, MMP-7, MMP-13, MMP-8, TIMP-1, TIMP-2, and TIMP-4. Thus, the method can comprise measuring MMP-2 and MMP-9; MMP-2 and MMP-13; MMP-13 and TIMP-1; MMP-13 and TIMP-2; MMP-13 and TIMP-4; MMP-2, MMP-13 and TIMP-1; MMP-2, MMP-13 and TIMP-2; MMP-2, MMP-13 and TIMP-4; or MMP-2, MMP-13, TIMP-1, TIMP-2, and TIMP-4. Other combinations of these analytes are contemplated and disclosed herein.

For example, when combined with a reduced level of MMP-13, increased TIMP-1 (e.g., TIMP-1>1200 ng/mL) can detect DHF. As another example, when combined with a reduced level of MMP-13 and increased TIMP-1, an amount of TIMP-4 greater than 3 ng/mL indicates LVH and predicts DHF. Thus, a method of detecting LVH and predicting diastolic heart failure in a subject, comprises measuring in a body fluid from the subject the profiles of MMP-13, TIMP-1, and TIMP-4. The profiles wherein the amount of MMP-13 is undetectable, the amount of TIMP-1 is about 50% greater than normal value (or greater than 1200 ng/mL) and the amount of TIMP-4 is at least about 50% greater than normal value (or greater than 3 ng/mL) are predictive of DHF.

The method can further comprise calculating the ratio of one or more of the MMPs or TIMPs to other MMPs or TIMPs. For example, the method can comprise calculating the ratio of MMP-9 to TIMP-1, TIMP-2 or TIMP-4.

In some aspects, a ratio of MMP-9/TIMP-1 plasma levels less than the normal value is an indication of LVH. For example, a ratio of MMP-9/TIMP-1 at least about 50% less than the normal mean value can be an indication of LVH. For example, in some aspects, a ratio of MMP-9/TIMP-1 plasma levels less than about $7 \times 10^3$, including less than about $7 \times 10^3$, $6 \times 10^3$, $5 \times 10^3$, $4 \times 10^3$, $5 \times 10^3$, $6 \times 10^3$, $1 \times 10^3$ is an indication of LVH.

In some aspects, a ratio of MMP-9/TIMP-2 plasma levels less than the normal value is an indication of LVH. For example, a ratio of MMP-9/TIMP-2 at least about 50% less than the normal mean value can be an indication of LVH. In some aspects, a ratio of MMP-9/TIMP-2 plasma levels less than about $100 \times 10^3$, including less than about $100 \times 10^3$, $90 \times 10^3$, $80 \times 10^3$, $70 \times 10^3$, $60 \times 10^3$, $50 \times 10^3$, $40 \times 10^3$, $30 \times 10^3$, $20 \times 10^3$, or $10 \times 10^3$, is an indication of LVH.

In some aspects, a ratio of MMP-9/TIMP-4 plasma levels less than the normal value is an indication of LVH. For example, a ratio of MMP-9/TIMP-4 at least about 50% less than the normal mean value can be an indication of LVH. In some aspects, a ratio of MMP-9/TIMP-4 plasma levels less than about 3, including less than about 3.0, 2.5, 2.0, 1.5, 1.0, 0.9, 0.8, 0.7, 0.6, 0.5, 0.4, 0.3, 0.2, 0.1, 0.05, or 0.01, is an indication of LVH.

In some aspects, a ratio of MMP-9/TIMP-1 plasma levels less than about $5 \times 10^3$, a ratio of MMP-9/TIMP-2 plasma levels less than about $100 \times 10^3$ and a ratio of MMP-9/TIMP-4 plasma levels less than about 1 is an indication of LVH.

In some aspects, MMP-2 plasma levels less than about 1000 ng/ml, MMP-13 plasma levels less than about 5 ng/ml, a ratio of MMP-9/TIMP-1 plasma levels less than about $5 \times 10^3$ a ratio of MMP-9/TIMP-2 plasma levels less than about $100 \times 10^3$ and a ratio of MMP-9/TIMP-4 plasma levels less than about 1 is an indication of LVH.

11. Prognosis

Also provided is a method of prognosis of diastolic heart failure that can be used, for example, with a subject who has been picked up on screening and then through a further plasma profile, is confirmed to have severe LVH and be at risk for developing DHF. In this case, the MMP-13 level will be quantified as well as TIMP levels. A low/undetectable MMP-13 level (0-5 ng/mL) coupled with high TIMP levels (such as TIMP-1>1200 ng/mL, TIMP-2>700 ng/mL, and/or TIMP-4>3 ng/mL) in comparison to reference normal subjects coupled with TIMP levels will likely yield critical insight into the degree of myocardial fibrosis and diastolic dysfunction. This holds prognostic value as to the progression of symptoms and hospitalization. Specifically, these patients can be more aggressively treated with hypertensive medications, and have more regular cardiovascular imaging studies.

For example, provided is a method of identifying a subject at increased risk for developing diastolic heart failure (DHF), comprising measuring MMP and/or TIMP levels in a tissue or bodily fluid of the subject and comparing said levels to reference values.

In some aspects, MMP-2 plasma levels less than the normal value is an indication of increased risk for developing diastolic heart failure. For example, an amount of MMP-2 at least about 20% less than the normal mean value can be an indication of increased risk for developing diastolic heart failure. In some aspects, MMP-2 plasma levels less than about 500 ng/ml, including less than about 500, 450, 400, 350, 300, 250, 200, 250, or 100 ng/ml, is an indication of increased risk for developing diastolic heart failure.

In some aspects, undetectable MMP-13 plasma levels is an indication of increased risk for developing diastolic heart failure. In some aspects, MMP-13 plasma levels less than about 10 ng/ml, including less than about 10, 9, 8, 7, 6, 5, 4, 3, 2, or 1 ng/ml, is an indication of increased risk for developing diastolic heart failure.

In some aspects, TIMP-1 plasma levels greater than the normal value is an indication of increased risk for developing diastolic heart failure. For example, an amount of TIMP-1 at least about 50% greater than the normal mean value can be an indication of increased risk for developing diastolic heart failure. In some aspects, TIMP-1 plasma levels greater than about 1000 ng/ml, including greater than about 1000, 1010, 1020, 1030, 1040, 1050, 1060, 1070, 1080, 1090, 1100, 1150, 1200, 1250, 1300, 1350, 1400, 1500, 1600, 1700, 1800, 1900, or 2000 ng/ml, is an indication of increased risk for developing diastolic heart failure.

In some aspects, TIMP-2 plasma levels greater than the normal value is an indication of increased risk for developing diastolic heart failure. For example, an amount of TIMP-2 at least about 50% greater than the normal mean value can be an indication of increased risk for developing diastolic heart failure. In some aspects, TIMP-2 plasma levels greater than about 50 ng/ml, including greater than about 50, 55, 60, 65, 70, 75, 80, 85, 90, 95, 100, 110, 120, 130, 140, 150, 160, 170, 180, 190, or 200 ng/ml, is an indication of increased risk for developing diastolic heart failure.

In some aspects, TIMP-4 plasma levels greater than the normal value is an indication of increased risk for developing diastolic heart failure. For example, an amount of TIMP-4 at least about 50% greater than the normal mean value can be an indication of increased risk for developing diastolic heart failure. In some aspects, TIMP-4 plasma levels greater than about 2 ng/ml, including greater than about 2, 3, 4, 5, 6, 7, 8, 9, 10, 15, 20, 25, 30, 35, 40, 45, or 50 ng/ml, is an indication of increased risk for developing diastolic heart failure.

In some aspects, MMP-9 plasma levels within normal range is an indication of increased risk for developing diastolic heart failure. In some aspects, MMP-7 plasma levels within normal range is an indication of increased risk for developing diastolic heart failure. In some aspects, MMP-8 plasma levels within normal range is an indication of increased risk for developing diastolic heart failure.

The method can further comprise measuring plasma levels of two or more MMPs and/or TIMPs. For example, the method can comprise measuring two, three, four, five, six, seven, or eight of MMP-2, MMP-9, MMP-7, MMP-13, MMP-8, TIMP-1, TIMP-2, and TIMP-4. Thus, the method can comprise measuring MMP-2 and MMP-9, MMP-2 and MMP-7, MMP-2 and MMP-13, MMP-2 and MMP-8, MMP-2 and TIMP-1, MMP-2 and TIMP-2, MMP-2 and TIMP-4, MMP-9 and MMP-7, MMP-9 and MMP-13, MMP-9 and MMP-8, MMP-9 and TIMP-1, MMP-9 and TIMP-2, MMP-9 and TIMP-4, MMP-7 and MMP-13, MMP-7 and MMP-8, MMP-7 and TIMP-1, MMP-7 and TIMP-2, MMP-7 and TIMP-4, MMP-13 and MMP-8, MMP-13 and TIMP-1, MMP-13 and TIMP-13, MMP-13 and TIMP-4, MMP-8 and TIMP-1, MMP-8 and TIMP-2, MMP-8 and TIMP-4, TIMP-1 and TIMP-2, TIMP-1 and TIMP-4, TIMP-2 and TIMP-4. Thus, the method can comprise measuring MMP-2, MMP-13 and TIMP-1; MMP-2, MMP-13 and TIMP-2; MMP-2, MMP-13 and TIMP-4; MMP-13, TIMP-1, and TIMP-2; MMP-13, TIMP-1, and TIMP-4; MMP-13, TIMP-2, and TIMP-4. Thus, the method can comprise measuring MMP-2, MMP-13, TIMP-1, and TIMP-2; MMP-2, MMP-13, TIMP-1, and TIMP-4; MMP-2, MMP-13, TIMP-2, and TIMP-4; MMP-13, TIMP-1, TIMP-2, and TIMP-4; MMP-2, TIMP-1, TIMP-2, and TIMP-4. Thus, the method can comprise measuring MMP-2, MMP-13, TIMP-1, TIMP-2, and TIMP-4. Other combinations of these analytes are contemplated and disclosed herein.

For example, provided is a method of detecting diastolic heart failure in a subject, comprising measuring in a body fluid from the subject an amount of MMP-13, TIMP-1, TIMP-4 and MMP-9. Also provided is a method of predicting diastolic heart failure in a subject, comprising measuring in a body fluid from the subject an amount of MMP-13, TIMP-1, TIMP-4 and MMP-9. In these methods, the profiles can show an amount of MMP-13 that is undetectable (or less than 10 ng/mL), an amount of TIMP-1 that is about 50% greater than normal value or greater than 1200 ng/mL, an amount of TIMP-4 that is at least about 50% greater than normal value or greater than 3 ng/mL and an amount of MMP-9 that is at least about 50% greater than normal value can detect LVH and DHF.

Also provided is a method of detecting diastolic heart failure in a subject, comprising measuring in a body fluid from the subject an amount of MMP-13, TIMP-1, TIMP-4 and MMP-2. Also provided is a method of predicting diastolic heart failure in a subject, comprising measuring in a body fluid from the subject an amount of MMP-13, TIMP-1, TIMP-4 and MMP-2. In these methods, the profiles can show an amount of MMP-13 that is undetectable (or less than 10 ng/mL), an amount of TIMP-1 that is about 50% greater than normal value (or greater than 1200 ng/mL), an amount of TIMP-4 that is at least about 50% greater than normal value (or greater than 3 ng/mL) and the amount of MMP-2 is at least about 20% less than normal value (or less than 1200 ng/mL).

The method can further comprise calculating the ratio of one or more of the MMPs or TIMPs to other MMPs or TIMPs. For example, the method can comprise calculating the ratio of MMP-9 to TIMP-1, TIMP-2 or TIMP-4.

In some aspects, a ratio of MMP-9/TIMP-1 plasma levels less than the normal value is an indication of LVH. For example, a ratio of MMP-9/TIMP-1 at least about 50% less than the normal mean value can be an indication of increased risk for developing diastolic heart failure. For example, in some aspects, a ratio of MMP-9/TIMP-1 plasma levels less than about $7\times10^3$, including less than about $7\times10^3$, $6\times10^3$, $5\times10^3$, $4\times10^3$, $5\times10^3$, $6\times10^3$, $1\times10^3$, $9\times10^2$, $8\times10^3$, $7\times10^2$, $6\times10^2$, $5\times10^2$, $4\times10^2$, $3\times10^3$, $2\times10^2$, or $1\times10^2$, is an indication of increased risk for developing diastolic heart failure.

In some aspects, a ratio of MMP-9/TIMP-2 plasma levels less than the normal value is an indication of LVH. For example, a ratio of MMP-9/TIMP-2 at least about 50% less than the normal mean value can be an indication of LVH. In some aspects, a ratio of MMP-9/TIMP-2 plasma levels less than about $100\times10^3$, including less than about $100\times10^3$, $90\times10^3$, $80\times10^3$, $70\times10^3$, $60\times10^3$, $50\times10^3$, $40\times10^3$, $30\times10^3$, $20\times10^3$, $10\times10^3$, $9\times10^3$, $8\times10^3$, $7\times10^3$, $6\times10^3$, $5\times10^3$, $4\times10^3$, $3\times10^3$, $2\times10^3$, or $1\times10^3$, is an indication of LVH.

In some aspects, a ratio of MMP-9/TIMP-4 plasma levels less than the normal value is an indication of LVH. For example, a ratio of MMP-9/TIMP-4 at least about 100% less than the normal mean value can be an indication of LVH. In some aspects, a ratio of MMP-9/TIMP-4 plasma levels less than about 1, including less than about 1, 0.9, 0.8, 0.7, 0.6, 0.5, 0.4, 0.3, 0.2, 0.25, 0.2, 0.15, 0.10, 0.05, or 0.01, is an indication of LVH.

Thus, provided is a method of detecting or predicting diastolic heart failure in a subject, comprising detecting a reduction in the ratio of MMP-9 to TIMP-4 in a body fluid from the subject compared to the normal ratio is provided. The method involves measuring a reduction in the ratio of at least about 50% compared to the normal ratio.

In some aspects, a ratio of MMP-9/TIMP-1 plasma levels less than about $5\times10^3$, a ratio of MMP-9/TIMP-2 plasma levels less than about $100\times10^3$ and a ratio of MMP-9/TIMP-4 plasma levels less than about 1 is an indication of LVH.

In some aspects, MMP-2 plasma levels less than about 1000 ng/ml, MMP-13 plasma levels less than about 5 ng/ml, a ratio of MMP-9/TIMP-1 plasma levels less than about $5\times10^3$ a ratio of MMP-9/TIMP-2 plasma levels less than about $100\times10^3$ and a ratio of MMP-9/TIMP-4 plasma levels less than about 1 is an indication of LVH.

12. Guiding Therapeutic Interventions

With respect to treatment, low MMP-13 and high TIMP levels could be monitored as an indicator of pharmacological efficacy. There are several relevant clinical scenarios for which this would be highly applicable. For example, while a hypertensive patient may have blood pressure within "normal limits", MMP-13 remains suppressed and TIMP levels are increased. Up titration of certain hypertension medications could then be utilized to "normalize" these biological markers of myocardial fibrosis and diastolic heart failure. The goal of this approach would be to serially measure blood values of the MMPs and TIMPs shown in Table 3, and to increase medication in order to bring these profiles to within the normal reference range.

In hypertensive patients that have been identified to have increased heart mass (size) due to high blood pressure, MMP/TIMP profiles can be utilized to follow the adequacy of treatment. The specific profiles identified disclosed herein would be monitored and efficacy of treatment determined as these MMP/TIMP profiles moved towards the normal range.

The MMP/TIMP profiles are based on measurements of individual MMPs or TIMPs. The amounts of these can be measured by any means known to provide an acceptable indication of how much of any of these is present in the sample being analyzed. An example of a means of measuring is provided in the Examples. The process of measuring an amount of an analyte (e.g., MMP or TIMP) includes a measurement of no amount or an undetectable amount of the analyte. The techniques and approaches for measuring MMP and TIMPs which formed the basis of this method were based upon high sensitivity immunoassays. Several of these immunoassays were developed by this laboratory (i.e. TIMP-4 assay measurements).

The immunoassay approach which was standardized for providing the measurements shown in Table 1 were performed by an enzyme linked immuno-assay (ELISA). However, other more sensitive and rapid methods for measuring blood levels of MMPs and TIMPs have been performed by this laboratory and these include the use of a multiplex assay system. In this example, multiple analytes in volume-limited samples, such as plasma or other biological samples, can be measured using a bead-based multiplex sandwich immunoassay. This emergent technique for multiplex analysis is built on technology that combines the sensitivity of ELISA with flow cytometric detection, allowing for the specific measurement of up to 100 different analytes within a single sample of less than 50 µl. This approach will allow for the measurement of multiple MMPs and TIMPs in a small blood sample. This type of approach can be used for the diagnostic, prognostic, predictive and therapeutic monitoring applications that are described herein. Specifically, to measure analyte concentrations simultaneously, the microbeads are incubated with sample (i.e. blood sample) and allowed to form complexes with the specific analytes of interest (i.e. MMPs). Detection antibodies (biotinylated), specific for a second epitope on each analyte, are then added to the mixture and allowed to bind to the microbeads complexed with analyte. The mixture is then incubated with a fluorescent reporter molecule (streptavidin-phycoerythrin) and the entire sample is passed through a two-laser flow cytometric detector. One laser detects the precise fluorescence of the microbead which defines the specific analyte being examined, and the other laser detects the amount of reporter fluorescence which is directly proportional to the amount of analyte bound. This process has been applied to a number of MMPs and other analytes that hold potential bearing to the CHF process and these are shown in the FIG. 16 and Table 1. This is but one example of how single or multiple analytes can be measured with a very small blood sample. Other examples of measurements that have been performed by this laboratory with respect to MMP/TIMP analytes include radioimmunoassay and immunoblotting assays. These approaches are also antibody based.

13. Combination

The herein disclosed methods can further comprise detecting other markers of heart failure. For example, the herein disclosed methods can further comprise measuring NT-proBNP levels in a tissue or bodily fluid of the subject and comparing said levels to reference values. The herein disclosed methods can further comprise measuring Troponin-I levels in a tissue or bodily fluid of the subject and comparing said levels to reference values.

14. Timing of Measurements

As described below and elucidated in further examples for screening and therapeutic monitoring, the timing of measurements would be context specific. For screening, this can be anytime a subject is presenting for a medical examination. Examples of this would include annual physicals, health fairs, and screening through residential facilities. Thus, the disclosed diagnostic method can be used to diagnose a subject that presents with signs and symptoms of CHF, but the underlying cause for this presentation is difficult to determine.

Figure 9A:
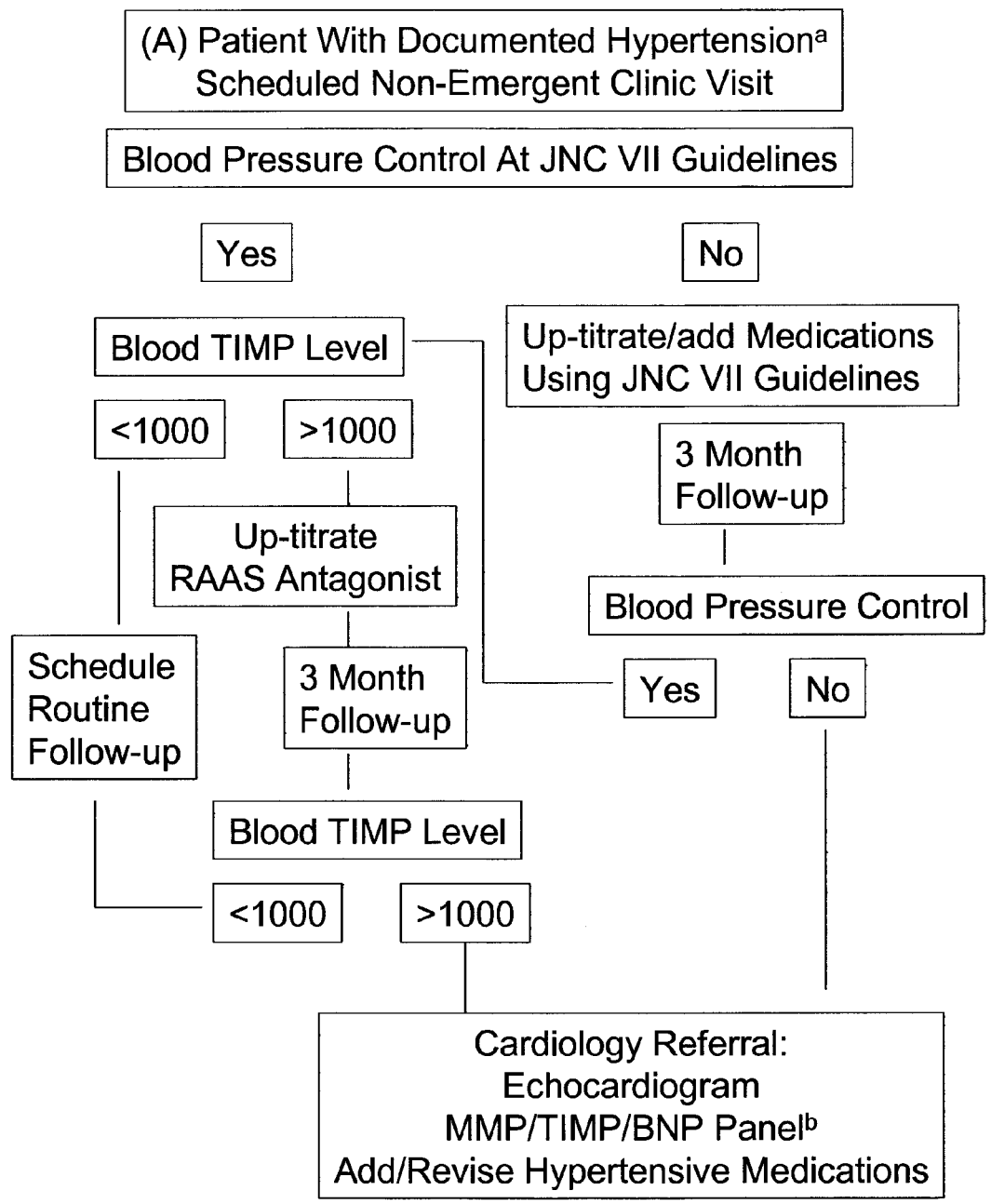
FIG. 9A shows schematic for treatment of patient with documented hypertension scheduled non-emergent clinic visit.
Figure 9B:
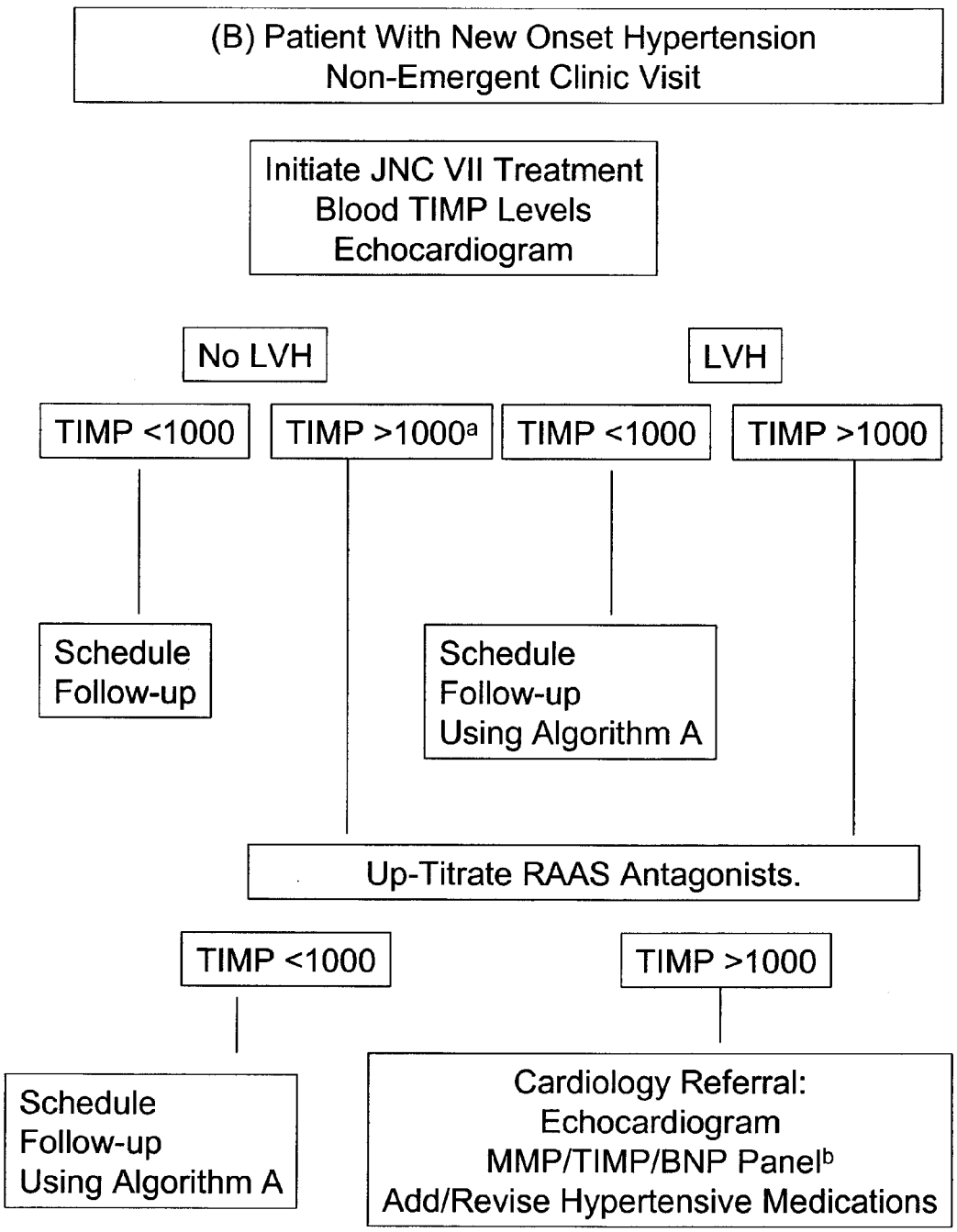
FIG. 9B shows schematic for treatment of patient with new onset hypertension non-emergent clinic visit.
Figure 9C:
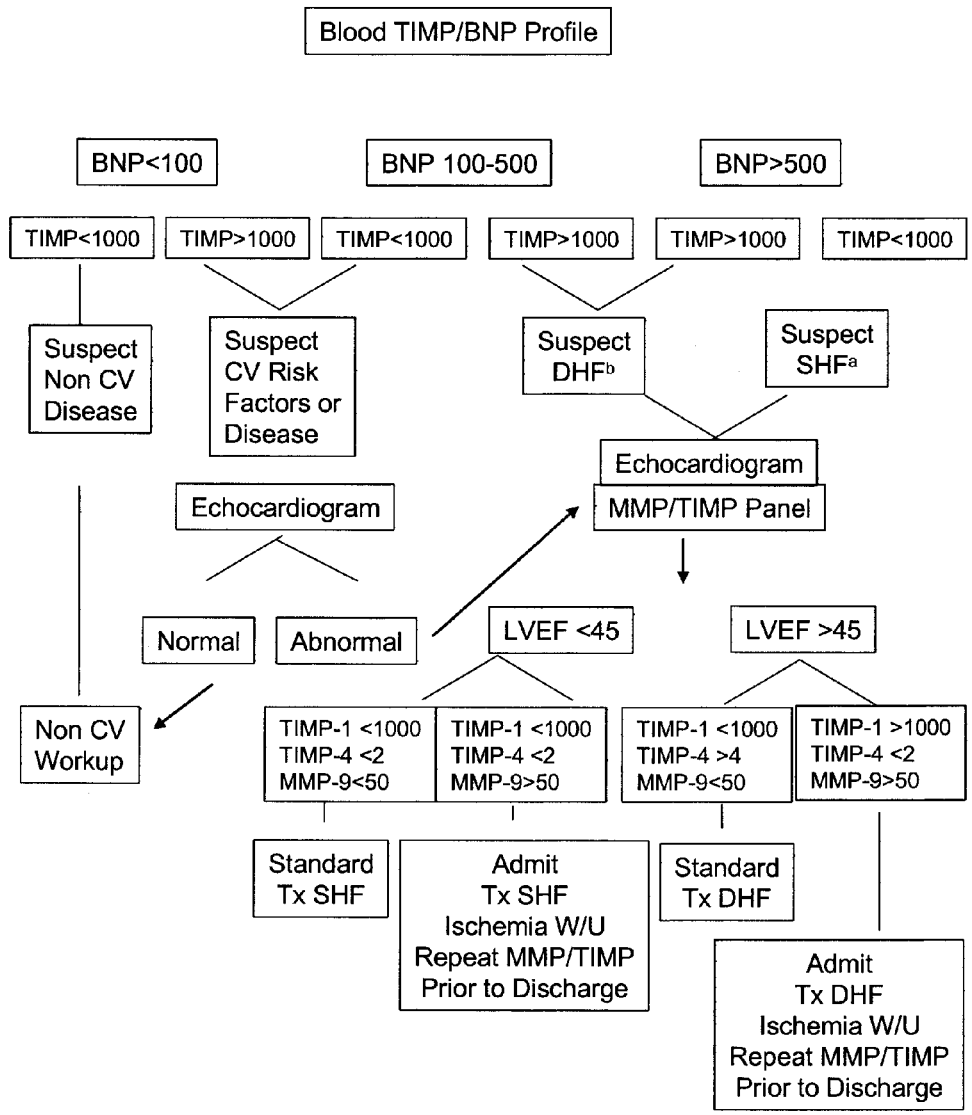
FIG. 9C shows schematic for treatment of patient presenting with signs or symptoms which might be caused by HF.

There are at least three initial time points for MMP/TIMP profiling for the methods disclosed herein. Initial measurements can be taken in a patient presenting for a routine clinic visit with history of established hypertension. Initial measurements can be taken at a health fair which would precipitate a clinic visit. Initial measurements can be taken in a patient presenting with symptoms due to hypertensive heart failure. The schematics in how the sampling and diagnostic approach for each of these scenarios is shown in FIGS. 9A-C for each of these cases.

Thus, the disclosed method of prognosis can be used to identify whether a subject that presents with high blood pressure (hypertension) has LVH or is at risk for developing DHF. The disclosed method of prognosis can also be used to identify whether a subject that presents with signs and symptoms of CHF has LVH and is at risk for developing of diastolic heart failure (DHF). For example, the method can be used with a patient that presents to the physician with complaints consistent with CHF. The physician can then apply the blood tests to determine whether an MMP/TIMP profile consistent with LVH and DHF is present. This would guide the physician into further diagnostic testing and treatment plans.

Another example of timing of blood sampling would be when a patient has been identified to have established LVH, then serially monitoring MMP/TIMP profiles could be used as predictive tools for the progression of DHF. These tests could be applied only once as a screening tool, or applied multiple times and sequentially in any given subject.

C. Kits

Disclosed herein are kits that are drawn to reagents that can be used in practicing the methods disclosed herein. The kits can include any reagent or combination of reagents discussed herein or that would be understood to be required or beneficial in the practice of the disclosed methods. For example, disclosed is a kit for assessing a subject's risk for developing DHF, in which components include components described in the previous section. For example, the components of an MMP/TIMP kit would include the necessary reagents for complexing to the relevant MMP and/or TIMP of interest (See Table 3 for list of relevant MMPs and TIMPs) to a detection reagent. In the example of an immunoassay approach, a fluorescently labeled antibody against a specific MMP or TIMP would be incubated with the blood sample and following a washing and non-specific binding clearance step, the amount of antibody bound to the MMP or TIMP of interest would be computed by measuring the relative degree of fluorescence. This can be a very simple kit which could be used for screening, or a more complex system where multiple MMP/TIMPs are measured from a single sample. A rationale for a graduated approach for measuring one MMP or TIMP of interest to measuring multiple MMP/TIMPs simultaneously has been described in a previous section. For a screening assay (i.e. MMP-13) the small blood sample would be processed into plasma (centrifugation) and the plasma mixed with the MMP-13 targeted antibody. The mixture would be centrifuged again, and the specifically bound antibody bound to MMP-13 would be read by a fluorimetry system. This equipment and measurement system could be easily fashioned into a small suitcase or table top system. The readout from the system would then indicate whether MMP-13 is below or above a specific threshold measurement (as defined in a previous section).

D. Examples

1. Example 1

Matrix Metalloproteinases/Tissue Inhibitors of Metalloproteinases: Relationship Between Changes in Proteolytic Determinants of Matrix Composition and Structural, Functional and Clinical Manifestations of Hypertensive Heart Disease Summary of Methods and Results: Plasma MMP-2,-9,-13, and TIMP-1,-2 and Doppler echocardiography were obtained in 103 subjects divided into 4 groups: a) reference subjects (CTL) with no evidence of cardiovascular disease, b) hypertension (HTN), controlled blood pressure, and no LV hypertrophy, c) hypertension, controlled blood pressure, with LV hypertrophy (HTN&LVH), but no CHF, d) hypertension, controlled blood pressure, LVH, and CHF (HTN&LVH&CHF). Compared with CTL, patients with HTN had no significant changes in any MMP or TIMP. Patients with HTN&LVH had decreased MMP-2 and MMP-13, and increased MMP-9. Only patients with HTN&LVH&CHF had increased TIMP-1. TIMP-1>1200 ng/mL was predictive of CHF.

Conclusion: Patients with hypertension but normal LV structure and function had normal MMP/TIMP profiles. Changes in MMP profiles which favor decreased ECM degradation were associated with LV hypertrophy and diastolic dysfunction. Increased TIMP-1 predicted the presence of CHF. These data indicate that changes in MMP/TIMP balance play an important role in the structural, functional and clinical manifestations of hypertensive heart disease.

Methods

Subjects: Two groups of subjects were recruited into this study: reference controls and patients with LVH. Reference controls were identified from locally sponsored health fairs and volunteers from the Medical University of South Carolina staff. Of the reference controls screened, 35% were enrolled, 50% had one of the exclusion criteria listed below and 15% declined participation. LVH patients were identified from echocardiographic studies. Of the patient echocardiograms screened, 10% were enrolled, 75% had one of the exclusion criteria listed below and 15% declined participation. There were some exclusion criteria common to both groups:

1) history of myocardial infarction, 2) regional wall motion abnormality, 3) coronary revascularization surgery, 4) amyloidosis, sarcoidosis, HIV, hypertrophic obstructive cardiomyopathy, valvular heart disease, 5) ejection fraction <50%, 6) malignancy, 7) significant renal or hepatic dysfunction, 8) rheumatological disease, 9) blood pressure >140/90 mmHg.

One hundred and three subjects were enrolled in this study: 53 reference control subjects and 50 subjects with evidence of LVH [LV wall thickness of >1.2 cm and/or LV mass index≥125 gm/m$^2$ (Table 4)]. The reference control subjects were subdivided into two groups based on the presence or absence of hypertension; 39 control subjects (referred to as "Reference control without hypertension"), had no history of hypertension, no evidence of cardiovascular (CV) disease, no symptoms or physical evidence of cardiovascular disease, no cardiovascular medication, and all echocardiographic measurements within the normal range (Table 5); and 14 patients (referred to as "Reference control with hypertension") had a history of arterial hypertension, controlled blood pressure (pharmacologically treated to meet JNC 7 criteria i.e., <140/90 mmHg), no left ventricular hypertrophy (Chobanian A V, et al. 2003) and, all echocardiographic measurements within the normal range (Table 5).

TABLE 4

Demographic, Left Ventricular Structure/Function and MMP/TIMP Data

|  | Reference Control | LVH |
|---|---|---|
| Number | 53 | 50 |
| Gender (male/female) | 20/33 | 24/26 |
| Age (years) | 59 ± 1 | 60 ± 2 |
| Systolic blood pressure (mmHg) | 127 ± 2 | 137 ± 3* |
| Diastolic blood pressure (mmHg) | 75 ± 1 | 76 ± 2 |
| End diastolic volume (ml/m$^2$) | 51 ± 2 | 52 ± 2 |
| Ejection fraction (%) | 66 ± 1 | 72 ± 2* |
| LV mass (gm/m$^2$) | 99 ± 3 | 162 ± 6* |
| Volume/mass ratio (ml/g) | 0.54 ± 0.02 | 0.32 ± 0.01* |
| Mitral E/A ratio | 0.95 ± 0.04 | 0.91 ± 0.05 |
| IVRT (msec) | 83 ± 2 | 91 ± 3* |
| E wave Deceleration time (msec) | 208 ± 8 | 234 ± 10* |
| Tissue doppler E' (cm/sec) | 10.1 ± 0.4 | 7.4 ± 0.4* |
| PCWP (mmHg) | 10 ± 1 | 16 ± 1* |
| MMP-2 (ng/ml) | 1387 ± 39 | 1205 ± 44* |
| MMP-9 (ng/mL) | 13 ± 3 | 26 ± 3* |
| TIMP-1 (ng/mL) | 997 ± 36 | 1291 ± 70* |
| TIMP-2 (ng/mL) | 44 ± 4 | 58 ± 7 |

Abbreviations:
Data are mean + SEM,
LV = Left Ventricular,
LVH = patients with hypertensive left ventricular hypertrophy,
Reference control = subjects with no evidence of cardiovascular disease,
IVRT = isovolumic relaxation time,
PCWP = pulmonary capillary wedge pressure,
MMP = matrix metalloproteinase,
TIMP = tissue inhibitor of MMP,
*= p < 0.05 compared with reference control.

TABLE 5

Reference Controls with and without Hypertension, LVH with and without CHF

|  | Reference Control without Hypertension | Reference Control with Hypertension | LVH without CHF | LVH with CHF |
|---|---|---|---|---|
| Number | 39 | 14 | 23 | 26 |
| Systolic Blood Pressure (mmHg) | 126 ± 3 | 131 ± 4 | 138 ± 3* | 133 ± 4 |
| Diastolic Blood Pressure (mmHg) | 74 ± 2 | 77 ± 2 | 82 ± 2* | 72 ± 2Δ |
| End Diastolic Volume (ml) | 97 ± 3 | 94 ± 5 | 98 ± 6 | 104 ± 5 |
| Ejection Fraction (%) | 65 ± 1 | 66 ± 1 | 70 ± 2* | 73 ± 2* |
| LV mass (gm/m2) | 94 ± 5 | 101 ± 3 | 160 ± 7*# | 164 ± 7*# |
| Mitral E/A ratio | 0.98 ± .05 | 0.85 ± 0.05 | 0.80 ± .09* | 0.97 ± 0.07Δ |
| Tissue Doppler E' (cm/sec) | 10.0 ± 0.4 | 9.8 ± 0.5 | 8.4 ± 0.4*# | 7.2 ± 0.5*#Δ |
| PCWP (mmHg) | 10 ± 1 | 11 ± 1 | 13 ± 2 | 17 ± 2*#Δ |
| PCWP/EDV (mmHg/ml) | 0.09 ± 0.01 | 0.11 ± 0.01 | 0.12 ± 0.01 | 0.17 ± 0.01*#Δ |

TABLE 5-continued

Reference Controls with and without Hypertension, LVH with and without CHF

|  | Reference Control without Hypertension | Reference Control with Hypertension | LVH without CHF | LVH with CHF |
|---|---|---|---|---|
| Ea (mmHg/ml) | 1.50 ± 0.05 | 1.61 ± 0.09 | 1.67 ± 0.10* | 1.45 ± 0.11Δ |
| MMP-2 (ng/ml) | 1383 ± 44 | 1399 ± 84 | 1119 ± 48*# | 1286 ± 73 |
| MMP-9 (ng/ml) | 13 ± 4 | 14 ± 5 | 27 ± 3*# | 24 ± 4*# |
| TIMP-1 (ng/ml) | 1000 ± 42 | 988 ± 76 | 1092 ± 77 | 1364 ± 86*#Δ |
| TIMP-2 (ng/ml) | 42 ± 4 | 48 ± 7 | 58 ± 11 | 59 ± 9 |

Abbreviations:
Data are mean + SEM,
LV = Left Ventricular,
PCWP = pulmonary capillary wedge pressure,
EDV = end diastolic volume,
Ea = effective arterial elastance,
MMP = matrix metalloproteinase,
TIMP = tissue inhibitor of MMP,
LVH = Left Ventricular Hypertrophy,
CHF = Chronic Heart Failure.
Significant differences amongst all 4 groups were analyzed using ANOVA and Tukey's multiple comparison tests,
*= p < 0.05 vs Reference control without Hypertension,
= p < 0.05 vs Reference control with Hypertension,
Δ= p < 0.05 vs LVH without CHF.

LVH patients were subdivided into two groups based on the presence or absence of CHF. 23 patients with hypertension, controlled blood pressure, with LVH, but no CHF were referred to as "LVH without CHF" (Table 5). The second sub-group consisted of 26 patients with hypertension, controlled blood pressure, LVH, and CHF and was referred to as "LVH with CHF". All these patients had evidence of CHF defined according to the Framingham criteria (Levy D, et al. 1996), evidence of abnormal relaxation (decreased E'), increased stiffness (increased PCWP and increased PCWP/EDV ratio), a markedly reduced 6 minute walk distance (979±86 feet in LVH with CHF group compared with 1839±60 feet, p<0.05 in the LVH without CHF group), EF ≥50%, and therefore, had diastolic heart failure.

Medications used to treat the hypertension were chosen and monitored by the patient's primary physician and not the investigators. These included diuretics, renin-angiotensin-aldosterone antagonists (angiotensin converting enzyme inhibitors, angiotensin II receptor blockers, and aldosterone blockers), direct vasodilators (nitrates, hydralazine), alpha adrenergic blockers, central nervous system blockers, aspirin, beta adrenergic receptor blockers, and calcium channel blockers. The mean duration of antihypertensive treatment was 6.4±1.5 years.

Echocardiographic Methods: Echocardiograms were performed using a Sonos 5500 system with an S-4 MHz transducer. Measurements were made using American Society of Echocardiography criteria (Sahn D J, et al. 1978; Schiller N B, et al. 1989). LV and left atrial volumes were calculated using the method of discs (Schiller N B, et al. 19). LV mass was calculated using the formula of Reichek and Devereux (Devereux R B, et al. 1986). Doppler measurements of mitral inflow E and A wave velocity, the E/A ratio, E wave deceleration time, and isovolumic relaxation time (IVRT) were made. Tissue Doppler (lateral mitral annulus) measurement of mitral E' and A' wave velocity were made. Pulmonary capillary wedge pressure (PCWP) was calculated using the formula: 2+1/3 E/E' (Nagueh S F, et al. 1998). Effective arterial elastance (Ea) was calculated using the formula: end systolic pressure/stroke volume.

MMP/TIMP Plasma Measurements: Gelatinases (MMP-2 and MMP-9), collagenase (MMP-13); and tissue inhibitors of MMPs (TIMP-1 and TIMP-2) were examined using 2-site enzyme-linked immunosorbent assay (ELISA) kits (Amersham Pharmacia Biotech, Buckimghamshire, UK). Plasma and the respective MMP standards were added to precoated wells containing the antibody to the MMP or TIMP of interest and washed. The resultant reaction was read at a wavelength of 450 nm (Labsystems Multiskan MCC/340, Helsinki, Finland). Because MMP-13 was found in very low levels in the plasma, the MMP-13 results were divided into detectable and non-detectable.

Statistical Analysis: MMP and TIMPs were measured every 2 hours for a 6 hour period in order to calculate a coefficient of variance for MMP/TIMP measurements between and within individual subjects in a subgroup of reference control subjects (n=20) using a one-way random effects ANOVA. Then the coefficient was calculated as the square root of the within person mean square error times 100. The intra-patient coefficient of variation for MMP-2=11.2±1.1%, TIMP-1=8.5±2.2% and TIMP-2=14.3±1.7%. An intra-assay coefficient of variation quantifying variation in the assay technique itself was less then 6% for all the MMP and TIMPs.

Initially, comparisons between reference controls versus LVH subjects were made using a 2-tailed Student t test. Subsequently, comparisons between all 4 groups (reference control with versus without hypertension versus LVH with versus without CHF) were analyzed using ANOVA and Tukey's multiple comparison tests. A p value of <0.05 was considered significant. Simple linear regression was used to examine the relationship between MMP and TIMP levels and measurements of LV structure and function. Mantel Hanzel chi square and receiver operating curves were used to evaluate the association between MMP-13 and TIMP-1 levels and presence of LVH and CHF. The potential effects of the medications on structure, function, or plasma data were examined first by a univariate then by a multivariate regression analysis. The structure, function, MMP, or TIMP measurement was the dependent variable with the medication entered as a dummy variable. A single drug was examined, and then drugs in combination were examined.

The research protocol used in this study was reviewed and approved by the institutional review board at the Medical University of South Carolina. Written informed consent was obtained from all participants. The authors had full access to the data and take responsibility for its integrity. All authors have read and agree to the manuscript as written.

Results

Reference Control Versus LVH

Structure/Function Data: The reference control subjects had a similar age and gender distribution as the LVH subjects (Tables 3 and 4). Compared to reference control, LVH had higher systolic blood pressure, significant concentric remodeling as evidenced by a 60% greater LV mass index, no difference in end diastolic volume, and a 40% lower LV end diastolic volume versus mass ratio. Compared to reference control, LVH had significant abnormalities in indices of LV diastolic relaxation and LV diastolic stiffness: increased IVRT, increased E wave deceleration time, decreased E', increased pulmonary capillary wedge pressure, and increased PCWP versus LV end diastolic volume ratio ($0.16 \pm 0.01$ mmHg/mL in LVH) compared to reference control ($0.09 \pm 0.01$ mmHg/mL, $p<0.05$), suggesting that there was an increase in the LV instantaneous end diastolic operating stiffness.

MMP and TIMP plasma profiles: Compared to reference control, MMP-2 was decreased and MMP-9 was increased in LVH. Significant differences were found in MMP-13 detectability (FIG. 1). Forty-seven percent of the reference control subjects had a detectable level of MMP-13, while MMP-13 was detectable in only 15% of the LVH subjects ($\chi^2=17.89$, $p<0.001$, odds ratio=0.24). Plasma TIMP-1 was significantly increased in LVH compared to reference control. TIMP-2 and the MMP-9/TIMP-1 and MMP-2/TIMP-2 ratios were not different between reference control and LVH.

Reference Control without Hypertension Versus Reference Control with Hypertension Structure/Function Data: Reference control subjects without hypertension served as the age and gender matched reference control group for comparison to the reference control with hypertension, the LVH without CHF, and the LVH with CHF groups. There were no significant differences in any demographic parameter or any echocardiographic measurement of LV structure or function between reference controls without hypertension versus reference control with hypertension (Tables 3 and 4). Left atrial maximum volume (LAMV) and emptying fraction (LAEF) were similar in reference control without hypertension (LAMV=$40 \pm 2$ ml, LAEF=$42 \pm 3\%$) compared to reference control with hypertension (LAMV=$42 \pm 4$ ml, LAEF=$43 \pm 2\%$).

MMP and TIMP plasma profiles: There were no significant differences in any MMP or TIMP plasma level between reference control subjects without hypertension versus reference control with hypertension.

LVH without CHF Versus LVH with CHF

Structure/Function Data: There were no significant differences in systolic blood pressure, LV volume, or mass between LVH without CHF and LVH with CHF subjects (Table 5). However, diastolic function was significantly more impaired in LVH with CHF compared to LVH without CHF. Indices of diastolic relaxation were slower, diastolic stiffness was greater and filling pressures were higher in LVH with CHF compared to LVH without CHF. In particular, in the LVH without CHF patients, tissue Doppler E' was decreased ($8.4 \pm 10.4$ cm/sec with 95% confidence intervals (CI) of 7.4, 9.3) compared with reference control without hypertension ($10 \pm 0.4$ cm/sec, 95% CI=9.3,11) and reference control with hypertension ($9.8 \pm 0.5$ cm/sec, 95% CI=8.1, 11). E' fell further in LVH with CHF ($7.2 \pm 0.5$ cm/sec, 95% CI=6.2, 8.3). In the LVH without CHF patients, PCWP was unchanged ($13 \pm 2$ mmHg, 95% CI=10.5, 15.2) compared with reference control without hypertension ($10 \pm 1$ mmHg, 95% CI=9.3, 10.6) and reference control with hypertension ($11 \pm 1$ mmHg, 95% CI=9.1, 12.2) but increased in LVH with CHF ($17 \pm 2$ mmHg, 95% CI=15.2, 17.7). The PCWP versus LV end diastolic volume ratio was not changed in the LVH without CHF patients but was significantly increased in the LVH with CHF patients. Effective arterial elastance was increased in LVH without CHF and was decreased in LVH with CHF. LAMV was increased in LVH without CHF (LAMV=$53 \pm 4$ ml, $p<0.05$ compared with reference control) and increased further in LVH with CHF (LAMV=$70 \pm 5$ ml, $p<0.05$ compared with LVH without CHF). LAEF was unchanged in the LVH with CHF (LAEF=$42 \pm 3\%$, $p<0.05$ compared with reference control) but increased in LVH with CHF (LAEF=$48 \pm 2\%$ compared with LVH without CHF).

MMP and TIMP plasma profiles: There were no significant differences in MMP-2, -9, -13, TIMP-2 or MMP/TIMP ratios in LVH without CHF compared to LVH with CHF (FIG. 1). However, TIMP-1 was significantly increased in LVH with CHF ($1364 \pm 86$ ng/ml, 95% CI=1185,1543) compared to LVH without CHF ($1092 \pm 77$ ng/ml, 95% CI=933,1252). In fact, TIMP-1 was elevated only in subjects with CHF. TIMP-1 was unchanged in the LVH without CHF patients compared with reference control without hypertension ($1000 \pm 42$ ng/ml, 95% CI=915,1085) and reference control with hypertension ($988 \pm 76$ ng/ml, 95% CI=824,1152).

Figure 2A:
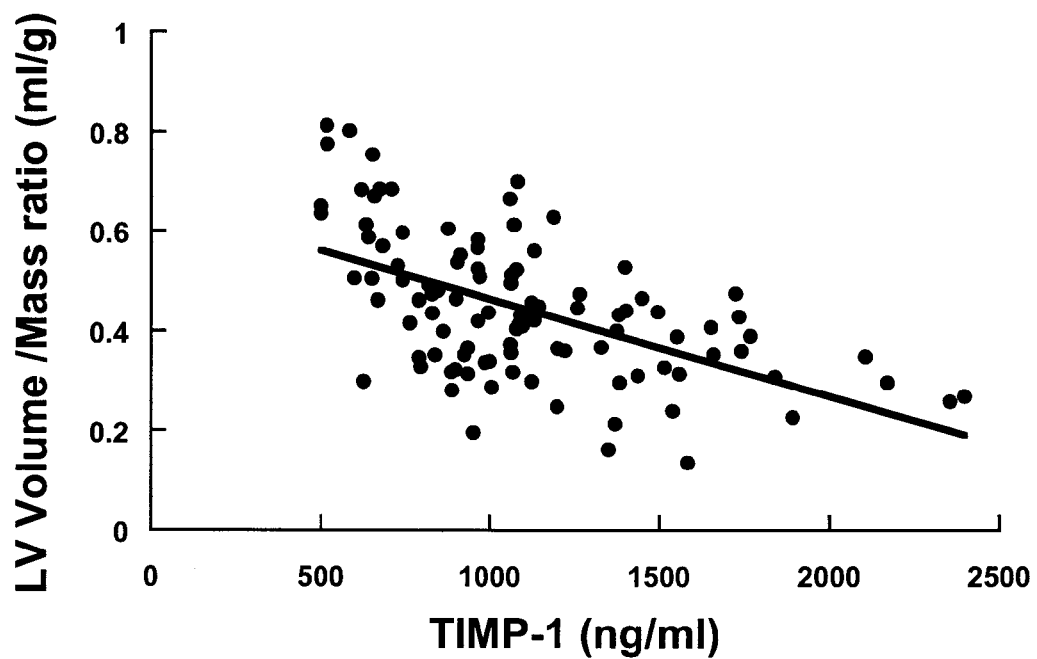
FIG. 2A shows relationship between tissue inhibitor of matrix metalloproteinase-1 (TIMP-1) and left ventricular (LV) volume/mass ratio. Higher levels of TIMP-1 were associated with lower values of LV volume/mass ratio indicating more pronounced concentric remodeling. r=−0.56, $p<0.05$.
Figure 2B:
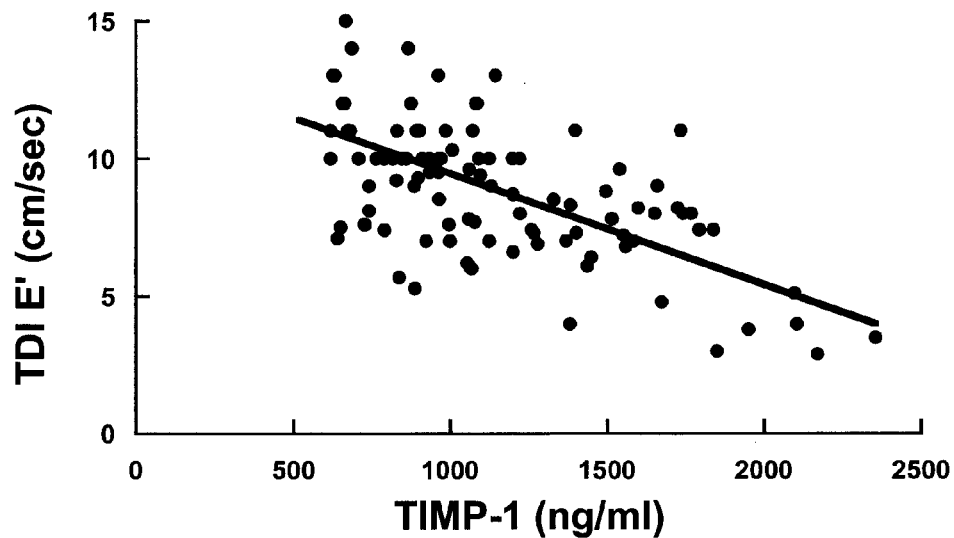
FIG. 2B shows relationship between tissue inhibitor of matrix metalloproteinase-1 (TIMP-1) and Tissue Doppler imaging (TDI) rapid filling wave (E'). Higher levels of TIMP-1 were associated with lower values of E'indicating slower LV diastolic relaxation rate. r=−0.41, $p<0.05$.
Figure 3:
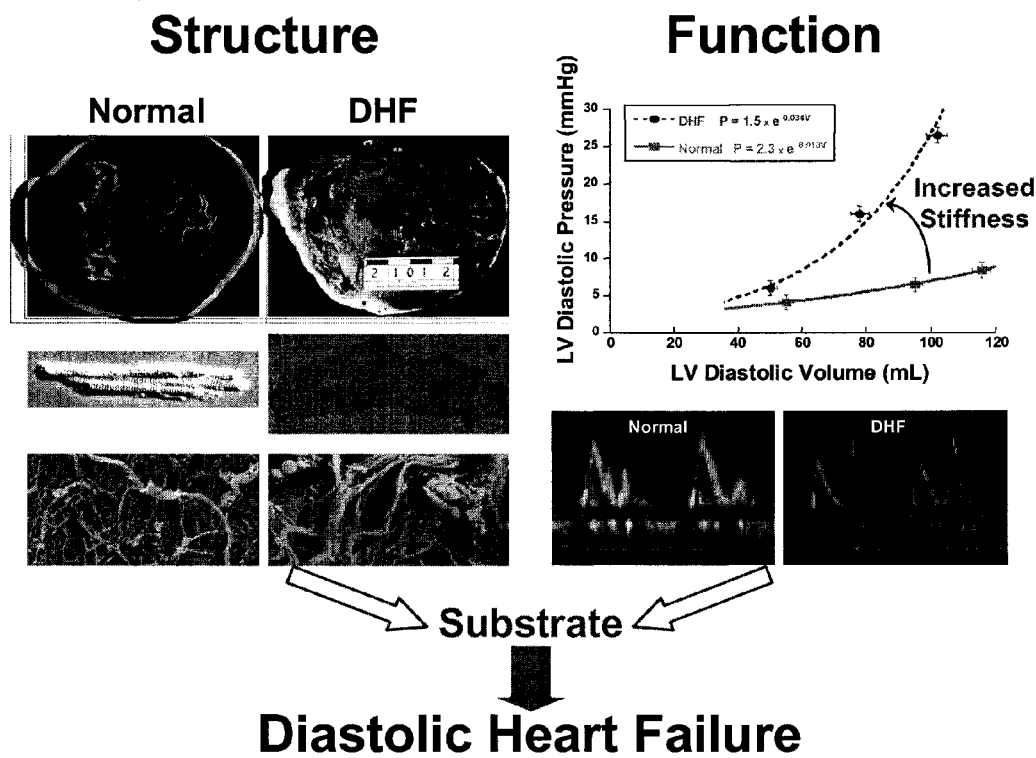
FIG. 3 shows structure and function of normal heart compared to heart with diastolic heart failure.
Figure 4A:
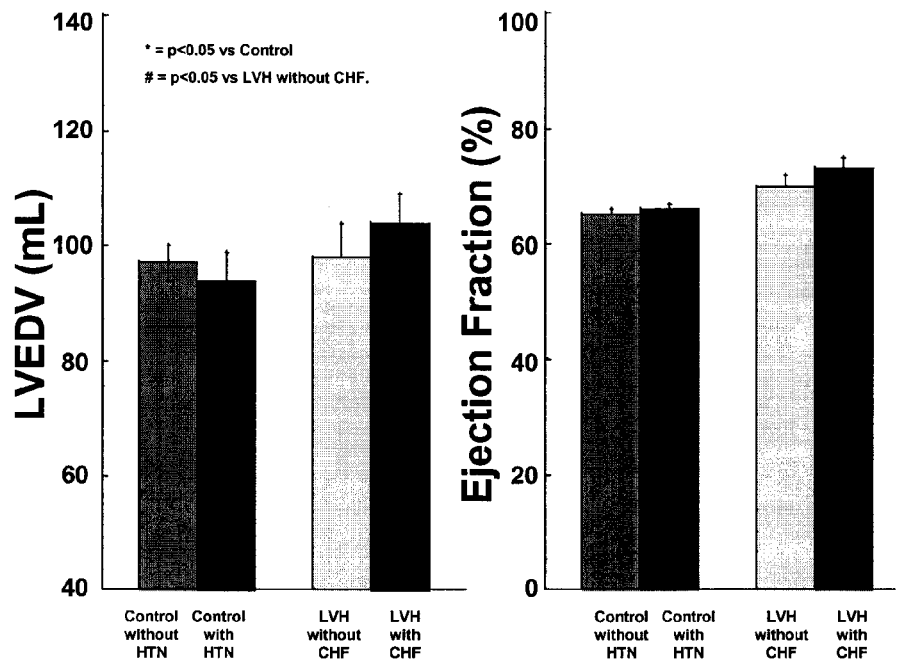
FIG. 4 shows results of echochardiography and MMP-9, MMP-2, and TIMP-1 plasma measurements for controls with and without hypertension (HTN) and subjects with ventricular hypertrophy with and without congestive heart failure (CGF).
Figure 4B:
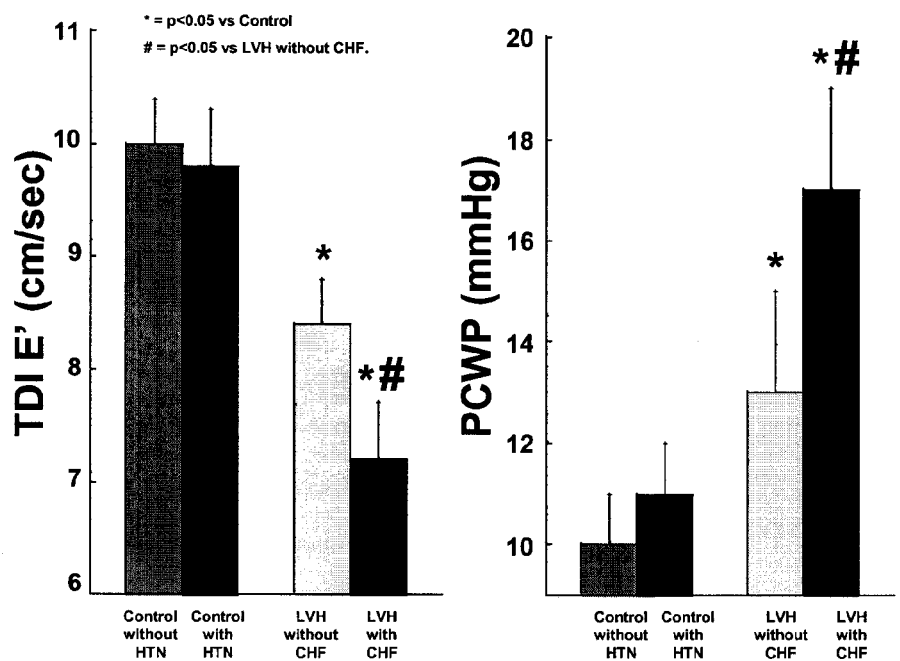
Figure 4C:
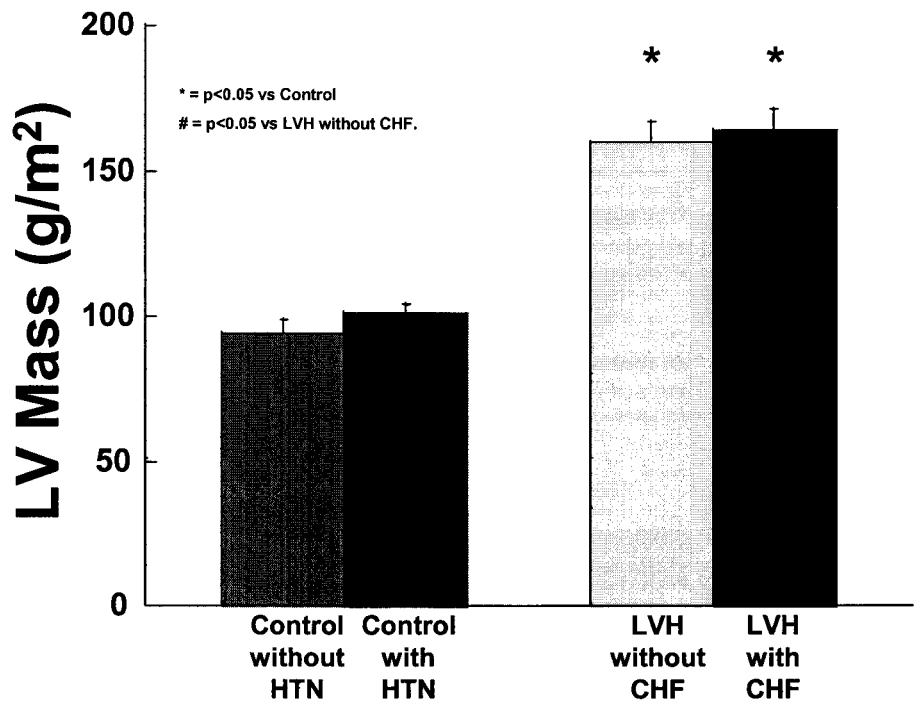
Figure 4D:
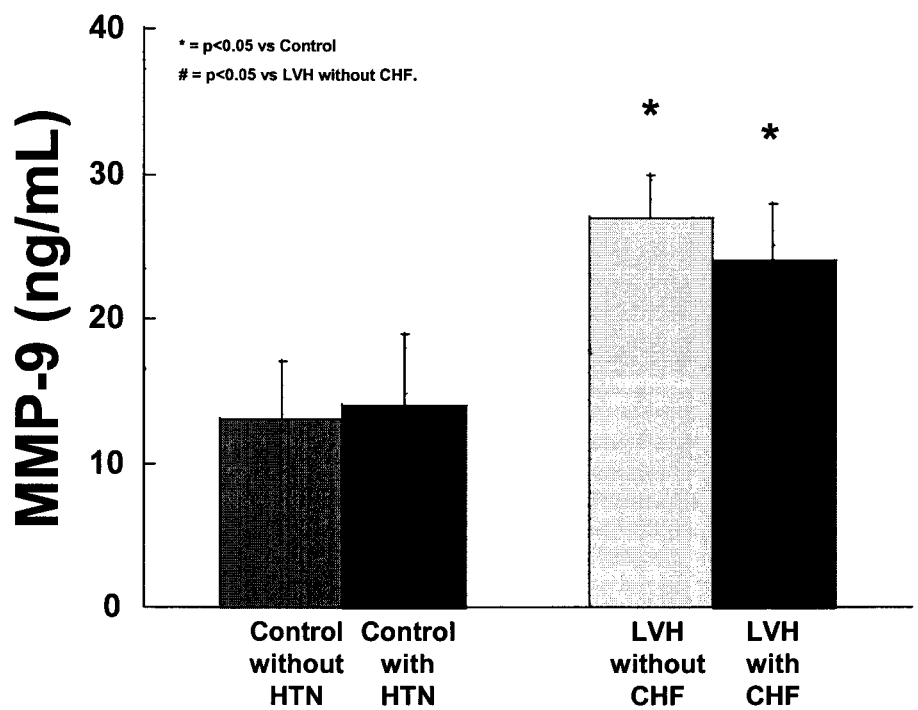
Figure 4E:
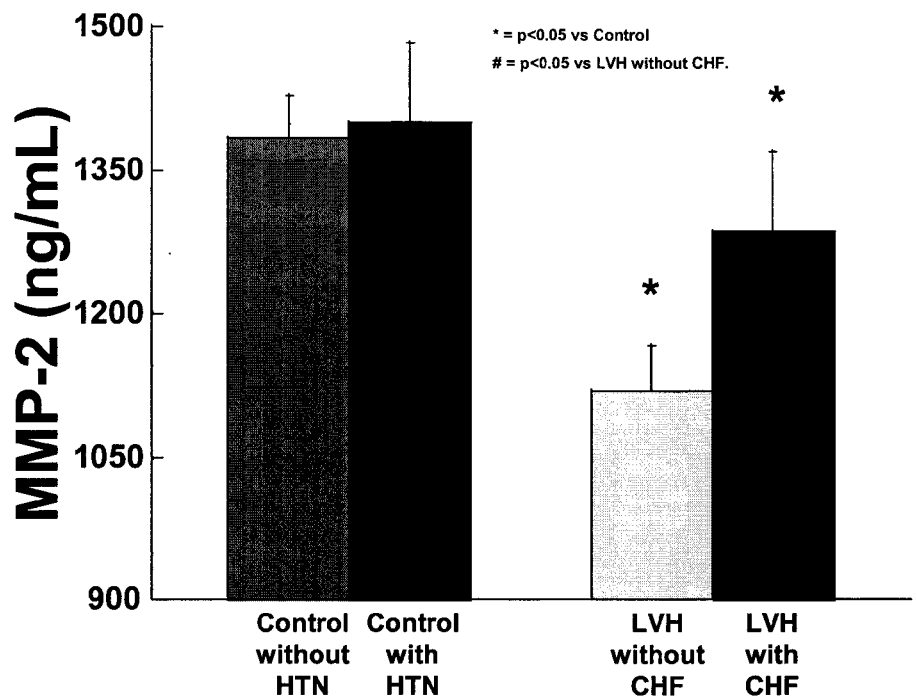
Figure 4F:
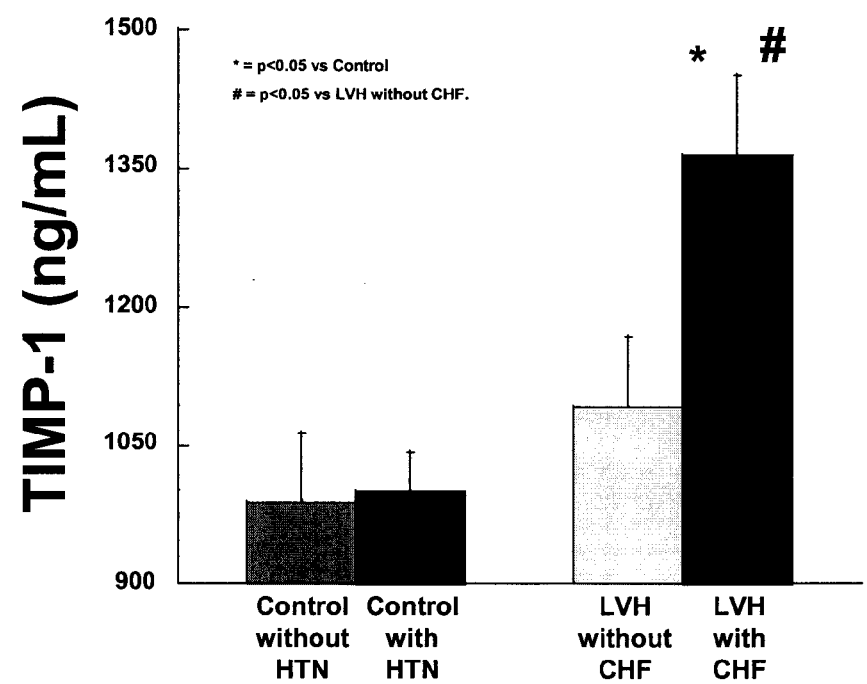
Figure 5:
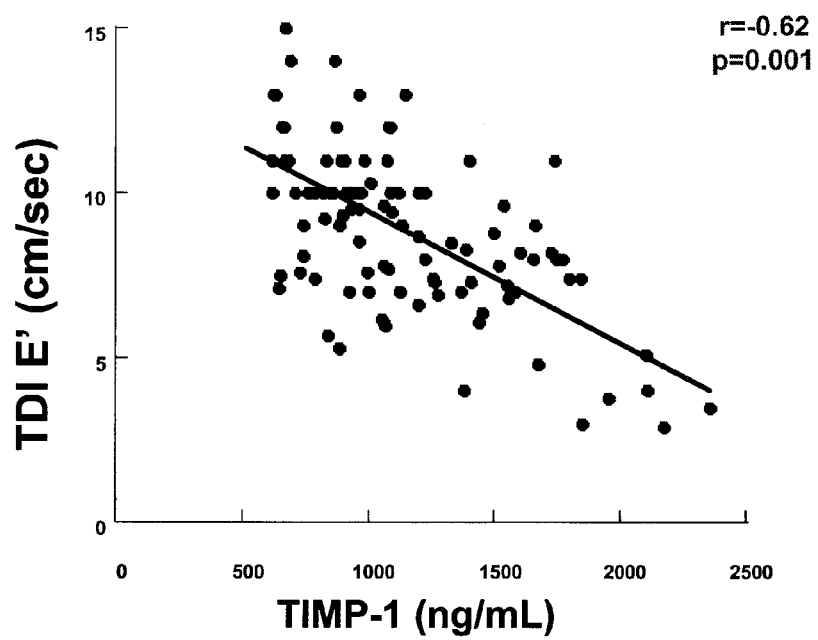
FIG. 5 shows Tissue Doppler imaging (TDI) rapid filling wave (E') relative to TIMP-1 levels.
Figure 6:
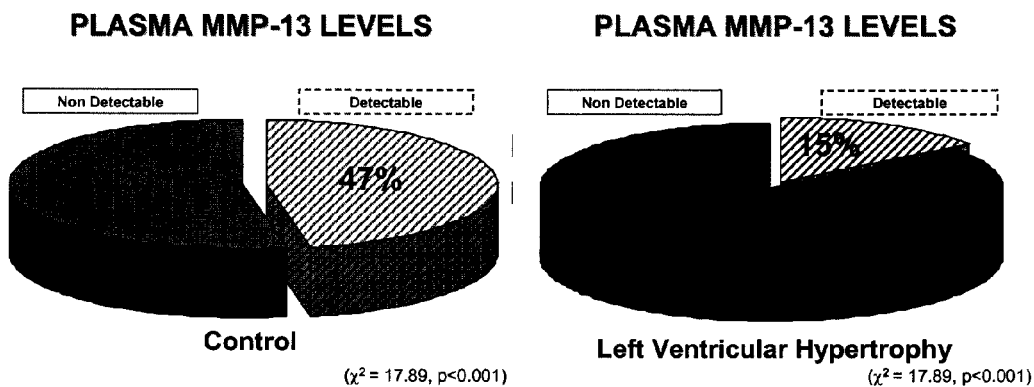
FIG. 6 shows plasma MMP-13 levels in controls and subjects with left ventricular hypertrophy.
Figure 7:
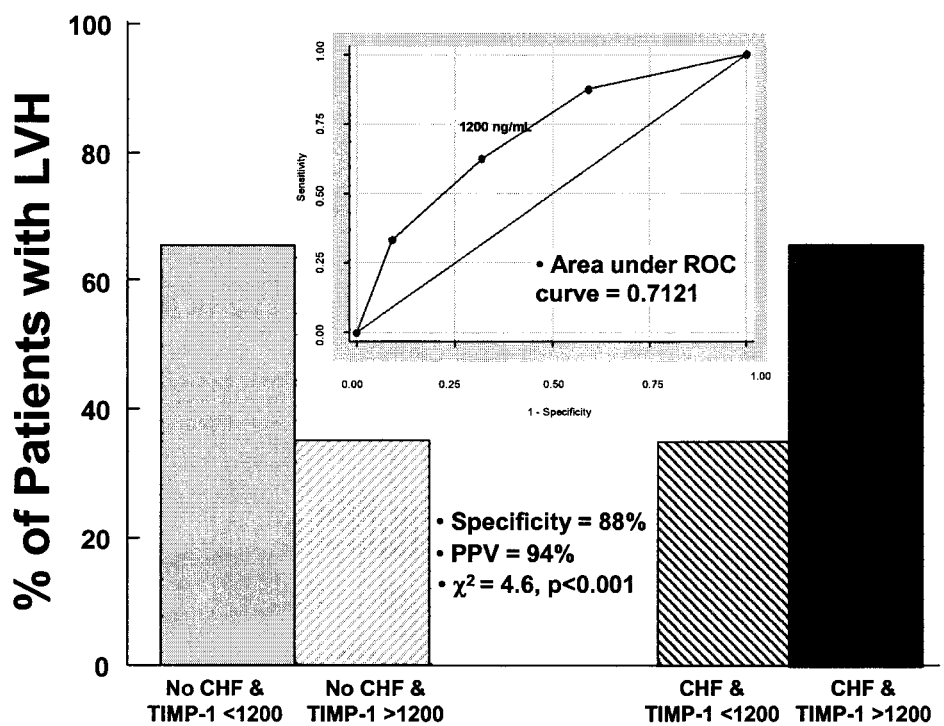
FIG. 7 shows the percentage of patients with or without congestive heart failure and with plasma TIMP-1 levels greater than or less than 1200 ng/ml that also have left ventricular hypertrophy.

Relationship between MMP and TIMP plasma profiles and LV structure and function: There was a significant relationship between TIMP-1 and the extent of LV remodeling. As TIMP-1 increased, LV mass increased ($r=-0.30$, $p=0.005$) and the volume/mass ratio fell ($r=-0.56$, $p=0.001$, FIG. 2A). There was a significant relationship between TIMP-1 and the extent of diastolic dysfunction. As TIMP-1 increased, the mitral E/A ratio decreased ($r=-0.22$, $p<0.027$), E' fell ($r=-0.62$, $p=0.001$, FIG. 2B), and the PCWP increased ($r=0.28$, $p=0.013$). Finally, there is a significant relationship between extent of CHF and TIMP-1 levels. The mean value of TIMP-1 was higher in LVH subjects with CHF who were NYHA class III versus class II. Having a TIMP-1 level of >1200 ng/ml was predictive of having LVH with CHF ($\chi^2=4.6$, $p=0.03$, specificity=88% and positive predictive value=94%, odds ratio=3.54, 95% confidence intervals=1.08, 11.50). The area under the receiver operator curve (ROC) was 0.71.

There was no relationship between the use of a specific medication and differences in LV structure, function or plasma MMP/TIMP profiles between groups. Specifically, there were no differences in any MMP or TIMP level between patients grouped by any medication or combination of medications. None-the-less, it is recognized that this study was not powered sufficiently to completely address the effects of drugs on LV structure, function or plasma MMP/TIMP profiles. Therefore, these data and analysis must be interpreted with appropriate caution.

Discussion

There were 3 unique findings in this study: 1) patients with hypertension but normal LV structure and function had a normal MMP/TIMP profile, 2) changes in MMP and TIMP profiles which favor decreased ECM degradation (decreased MMP-2, -13, increased TIMP-1) were associated with LV hypertrophy and diastolic dysfunction, and 3) increased TIMP-1 predicted the presence of CHF.

While pleotropic in their substrates and actions, changes in myocardial MMPs and TIMPs have predictable effects on the ECM (Spinale, F G. 2002; Chapman R E, et al. 2004). For example, MMP-2 (a gelatinase) degrades basement membrane proteins, fibrillar collagen peptides, and newly synthesized collagen fibers. In the current study, MMP-2 was significantly decreased in patients with hypertensive LVH. MMP-9 (a gelatinase) has the same structural protein substrates as MMP-2 but has a much lower level of activity. However, MMP-9 has significant affects on important biologically active proteins/peptides such as TGF-☐, and other "pro-fibrotic" proteins and pathways. Activation of pro-fibrotic pathways by increased MMP-9 would be expected to increase ECM accumulation. Thus, the decreased MMP2 and increased MMP-9 levels found in the LVH patients in the current study may be one factor contributing to the observed structural and functional changes seen in hypertensive heart disease.

MMP-13 is a collagenase that is found in very low levels in the plasma and is difficult to quantify accurately even with a high sensitivity assay. Therefore, in the current study, rather then reporting MMP-13 as a quantitative value, the results were dichotomized. Detectable MMP-13 in the plasma of patients with LVH was greatly reduced and was further reduced in patients with LVH and CHF. The reduction in this collagenolytic enzyme would be expected to cause reduced fibrillar collagen turnover, reduced degradation, and increased ECM accumulation.

MMP activity is regulated at several levels that not only includes transcriptional regulation, but also includes post-translational modification such as TIMP binding. The TIMPs bind to active MMPs in a 1:1 relationship, inhibit MMP enzymatic activity and thereby form an important control point with respect to net ECM proteolytic activity (Spinale, F G. 2002; Chapman R E, et al. 2004; Brew K, et al. 2000). The current study showed that plasma levels of TIMP-1 increased in patients with LVH and CHF. As a result, the balance between MMPs and TIMPs was altered in favor of reduced ECM proteolytic activity which would therefore facilitate ECM accumulation. There are four known TIMPs, and the transcriptional regulation of these molecules is not homogeneous (Brew K, et al. 2000). Discordant levels of TIMPs have been observed in both animal models of heart failure and in patients with cardiomyopathic disease (Wilson E M, et al. 2002; Stroud R E. 2005). In the current study, a robust increase in TIMP-1 was observed in LVH patients with CHF. In contrast, only a small increase in TIMP-2 was observed in LVH patients either with or without CHF. These observations likely underscore the different functions and regulatory pathways for TIMPs in the LV remodeling process. A unique finding of the present study was that a specific type of TIMP, TIMP-1 was strongly associated with the development of CHF. In patients with LVH and CHF, it is not clear whether the increased TIMP-1 levels contributed to the development of CHF or was the result of its development. What is clear however, is that increased TIMP-1 was uniquely present in patients with LVH and CHF and plasma TIMP-1 values >1200 ng/ml was predictive of the presence of CHF. Therefore, this plasma analyte should be considered in the development of diagnostic criteria for heart failure with a normal ejection fraction (diastolic heart failure) and for design of novel therapeutic management strategies for diastolic heart failure. However, it is recognized that the partition value of TIMP-1=1200 ng/ml was chosen in a "post-hoc" rather then a prospective fashion. Therefore, the validity of its predictive value must be interpreted with appropriate caution and confirmed in additional studies which use a large, prospective serial study design.

The changes in MMP/TIMPs that occur in patients with hypertensive heart disease may effect growth regulation in both the extracellular and the cardiomyocyte compartments which together result in concentric LV hypertrophy and increased collagen content. Collagen homeostasis is determined by the balance between synthesis, post-translational modification and degradation. In hypertensive heart disease, Diez et al and others have shown that increased collagen content was associated with increased plasma markers of collagen synthesis, decreased collagen degradation and decreased collagen turnover (Diez J, et al. 2002; Lopez B, et al. 2001a; Lopez B, et al. 2001b). Changes in the MMP/TIMP profiles found in the current study disclose potential mechanisms by which changes in synthesis, degradation and turnover may take place.

While there are many determinants of LV structural remodeling, blood pressure is one of the most important. However, data from the current study indicate that even after blood pressure has been adequately controlled, ongoing changes in MMPs and TIMPs predict, probably determine, and are certainly associated with persistent concentric remodeling, LVH and diastolic heart failure. Regression of LVH requires appropriate remodeling of the ECM including degradation and turnover of ECM components (particularly the basement membrane proteins) and alterations the cardiomyocyte-matrix interactions. The current study showed that patients with hypertensive LVH had persistent abnormalities in specific MMP (decreased MMP-2) and TIMP (increased TIMP-1) profiles which would be expected to favor continued cardiomyocyte-basement membrane-matrix connections and not the ECM turnover necessary to accommodate LV mass regression. It seems likely therefore, that the ongoing changes in MMPs and TIMPs seen in the current study contribute to the phenotypic and structural changes present in hypertensive heart disease.

The current study utilized plasma levels of MMPs and TIMPs as surrogate markers to reflect changes in myocardial levels of these enzymes and peptides. MMP activation and TIMP binding is a compartmentalized process that occurs within the myocardial interstitium (Spinale, F G. 2002; Chapman R E, et al. 2004). Thus, plasma levels do not necessarily reflect the net ECM proteolytic activity that occurs within the myocardium. Differences in plasma MMP and TIMP levels observed between reference control and patients with hypertensive heart disease in the current study are likely to reflect differences at the myocardial level (Joffs C, et al. 2001; Yarbrough W M, et al. 2003; Lindsey M L, et al. 2003). It is possible that the myocardium is not the only source of MMPs and TIMPs in LVH patients. Therefore, measurements of plasma MMP and TIMP levels represent the summation of MMPs and TIMPs released from both cardiac as well as non-cardiac sources. However, the specific exclusion criteria utilized in the current study helped to eliminate significant changes in the major non-cardiac sources of MMPs and TIMPs. Never-the-less, it must be recognized that patients with hypertension and LVH, with or without chronic heart failure, may have changes in other non-cardiac tissues, such as the kidneys and the vasculature, that may contribute to MMP and TIMP release into the plasma. The findings of the current study demonstrate differences in plasma MMP and TIMP levels between reference control and LVH patients.

Conclusion: A specific pattern of changes in the ECM proteolytic system was associated with each structural, functional, and/or clinical manifestation of hypertensive heart disease. Subjects with adequately controlled blood pressure with no structural or functional changes in the left ventricle did not have any changes in the MMP/TIMP signature. However, patients with LVH in spite of adequate blood pressure control had decreased MMP-2 and -13. Increases in TIMP-1 were found in patients with LVH and CHF. In particular, the transition between hypertensive LVH and the development of CHF is heralded by changes in MMPs and TIMPs such as an increase in TIMP-1>1200 ng/ml or the absence of MMP-13. However, the current study had a limited sample size, used a cross-sectional design, and did not perform serial studies over time. These limitations mandate that our observations be further tested and confirmed using a large, prospective serial study design. None-the-less, the data from the current study indicate that the observed stochastic changes in MMP/TIMPs play an important role in the manifestations of hypertensive heart disease. Understanding this ECM dependent pathophysiology provides improved diagnosis and treatment of patients with hypertensive heart disease.

Clinical Perspective: Chronic arterial hypertension is a common cause of LV concentric hypertrophy, decreased relaxation rate and increased stiffness. The structural and functional changes caused by hypertension result from changes to both of the principle constituents of the myocardium, the cardiomyocyte and particularly the extracellular matrix (ECM). These LV structural and functional changes create the substrate necessary for the development of diastolic heart failure (DHF). However, what controls these changes in the ECM, whether blood pressure control alone can prevent or reverse these changes, and whether knowledge of the ECM-control mechanisms would aid diagnosis or treatment of hypertensive heart disease is unknown. The current study showed that changes in the pattern of specific ECM proteolytic proteins/peptides (MMPs and TIMPs) were associated with each structural, functional, and clinical manifestation of hypertensive heart disease. Subjects with adequately controlled blood pressure with no LV structural or functional changes did not have any changes in the MMP/TIMP signature. Therefore, treatment of hypertension can prevent changes in the ECM and the ECM proteolytic system. However, patients with residual or resistant LVH, in spite of adequate blood pressure control, had abnormal MMPs. The development of DHF was heralded by an increase in TIMP-1>1200 ng/ml. These data suggest that regression of LVH and prevention of DHF are dependent on more than just changes in blood pressure alone, and may need to target and normalize changes in MMP/TIMPs. Understanding this ECM dependent pathophysiology provides improved diagnosis and treatment of patients with hypertensive heart disease.

2. Example 2

Matrix Metalloproteinases/Tissue Inhibitors of Metalloproteinases: Relationship Between Changes in Proteolytic Determinants of Matrix Composition and Structural, Functional, and Clinical Manifestations of Hypertensive Heart Disease Methods Study Enrollment Table 6 shows the study enrollment. The exclusion criteria were a history of myocardial infarction, cardiomyopathy, valvular or wall motion abnormalities, arrhythmia, infiltrative cardiac disease, EF <50%, uncontrolled hypertension (SBP >140 or DBP >90), or systemic disease that affect MMP/TIMP plasma profiles. The inclusion criteria for controls and controls with HTN were men and women age 18-90 years without evidence of structural cardiovascular disease. The inclusion criteria for LVH and LVH with CHF were men and women age 18-90 years with established LV hypertrophy by echocardiography (wall thickness of >1.2 cm or LV mass Index >125 g/m).

TABLE 6

Study Enrollment

| | Control | | LVH | |
|---|---|---|---|---|
| | −HTN | +HTN | −CHF | +CHF |
| Number | 39 | 14 | 23 | 26 |
| Age | 59 ± 2 | 60 ± 2 | 56 ± 2 | 64 ± 2 |
| SBP (mmHg) | 126 ± 3 | 131 ± 4 | 138 ± 3 | 133 ± 4 |
| DBP (mmHg) | 74 ± 2 | 77 ± 2 | 82 ± 2 | 72 ± 2 |

Echocardiography measurements: standard to dimensional echocardiography was used.

Echocardiography calculations: LV volume was calculated by the method of discs. LV Mass was calculated by the Penn Method. PCWP was calculated as $2+1.3\times(E/Ea)$.

MMP/TIMP Plasma Measurements: Plasma measurements were obtained by enzyme-linked immunosorbent assay (ELISA) (Ammersham Pharmacia Biotech) for the gelatinases MMP-2 and MMP-9, the collagenase MMP-13, and the TIMPS TIMP-1 and TIMP-2.

Results

FIGS. 7-11 show the results of the study.

Conclusions

Patients with HTN but normal LV structure and function had a normal MMP/TIMP profile. Changes in MMP/TIMP profiles which favor decreased ECM degradation were associated with LV hypertrophy and diastolic dysfunction. Increased TIMP-1 predicted the presence of CHF. Changes in the myocardial extracellular matrix proteolytic system are measurable using plasma assays of selected MMPs and TIMPs. Each manifestation of hypertensive heart disease is associated with a specific pattern of changes in the ECM proteolytic system. Hypertensive patients with structural remodeling, diastolic dysfunction and/or clinical CHF are characterized by a decrease in the MMPs and an increase in TIMPs.

3. Example 4

Criteria for Differentiating, Predicting and Diagnosing Heart Failure in Patients with Hypertension Provided in Table 7, a clear set of normal values for human subjects within the age range and across genders is provided. There has been no previously compiled list of normal reference values for MMPs/TIMPs that are as inclusive as this and furthermore provides for normal reference ranges since age matched subjects, free from cardiovascular disease were included. Moreover, novel stoichiometric ratios for MMP/TIMP profiles are provided which will prove to hold important diagnostic and prognostic information as detailed in subsequent tables. These data were collected and analyzed from over 100 subjects.

TABLE 7

Normal Human* Reference Ranges

| MMP/TIMP Plasma Levels (ng/mL) | |
|---|---|
| MMP-2 | 1000-1500 |
| MMP-9 | 0-20 |
| MMP-7 | 0-5 |
| MMP-13 | 0-10 |
| MMP-8 | 0-3 |
| TIMP-1 | 800-1000 |

TABLE 7-continued

Normal Human* Reference Ranges

| | |
|---|---|
| TIMP-2 | 25-50 |
| TIMP-4 | 0-2 |
| MMP-9/TIMP Ratios | |
| MMP-9/TIMP-1 | 7-15 |
| MMP-9/TIMP-2 | 100-500 |
| MMP-9/TIMP-4 | 1-10 |

*Normal Adults Age 25-70 years

Table 8 presents the MMP and TIMP values in absolute terms, the MMP/TIMP ratios in absolute terms, and the percent changes from normal reference values based upon the absolute terms, in patients with well managed blood pressure, but carry a diagnosis of hypertension. These values were collected as described within the body of the original application. A unique plasma profile, which would not be predicted from past reports in animal studies or the limited clinical studies published previously is demonstrated. This unique profile includes a fall in MMP-2, no change in MMP-9, non-detectable (below sensitivity of any assay system currently used) for MMP-13, and robustly increased levels of TIMP-1. Moreover, an increase in the cardiovascular specific marker for TIMP-4 could be demonstrated. These changes in MMP and TIMP profiles are unique to patients with hypertension and demonstrate early changes occurring within the heart tissue of these patients. This unique and specific profile can be used to guide therapy in order to minimize these changes in MMP and TIMP profiles from normal subjects. Moreover, these plasma profiles can be used for generalized screening for at risk patient populations and identify patients that are at risk for future adverse events.

TABLE 8

Diagnostic for Hypertensive Heart Disease

| Plasma MMP/TIMP Levels (ng/mL)* | |
|---|---|
| MMP-2 | <1000 |
| MMP-9 | 25-50 |
| MMP-7 | 0-5 |
| MMP-13 | 0-5 |
| MMP-8 | 0-3 |
| TIMP-1 | >1000 |
| TIMP-2 | >50 |
| TIMP-4 | >2 |
| Plasma MMP/TIMP Ratios | |
| MMP-9/TIMP-1 | <5 |
| MMP-9/TIMP-2 | <100 |
| MMP-9/TIMP-4 | <3 |

*Patient diagnosed with high blood pressure and under proper medical management

Table 9 demonstrates plasma profiles for MMPs and TIMPs that emerge in patients with heart failure secondary to hypertensive heart disease. These data were compiled from studies provided in the initial application. This past study demonstrated that the differentiation of the presence and absence of heart failure in hypertensive patients could be obtained by the loss of a signal for MMP-13 and the robust increase in TIMP-1. In fact, receiver operator curves (ROC) for prediction and diagnosis for heart failure were provided previously. In marked contrast to patients with heart failure secondary to a myocardial infarction (heart attack), MMP-9 levels are normal or below normal. The differentiation between these two disease states is possible and provided in an upcoming table. Moreover, utilizing a cardiovascular specific marker, TIMP-4, it could be demonstrated that this was increased in patients with hypertensive heart disease and that this provided cardiovascular specificity to the plasma profile-never demonstrated previously. These data provide the first differential profile for identifying through plasma markers, patients suffering from heart failure due to hypertensive heart disease. This is an important issue as t treatment modalities differ based upon the underlying cause of the heart failure. How these new data could be used to guide therapy and clinical decision making was provided in the initial application.

TABLE 9

Hypertensive Patients at Increased Risk for Heart Failure*

| Plasma MMP/TIMP Levels (ng/mL) | |
|---|---|
| MMP-2 | <500 |
| MMP-9 | 0-20 |
| MMP-7 | 0-5 |
| MMP-13 | ND (not detectable) |
| MMP-8 | 0-3 |
| TIMP-1 | >1500 |
| TIMP-2 | >100 |
| TIMP-4 | >6 |
| Plasma MMP/TIMP Ratios | |
| MMP-9/TIMP-1 | <2 |
| MMP-9/TIMP-2 | <50 |
| MMP-9/TIMP-4 | <0.25 |

*Patient diagnosed with high blood pressure and under proper medical management

The unique plasma signature that was developed in this application and presented in the supporting material provides for the first time an ability to differentiate the underlying causes for a patient presenting for heart failure. Specifically, as shown in Table 10, a unique and very different plasma profile emerges from a patient at risk for developing, or presenting with heart failure secondary to a myocardial infarction or that in patients with heart failure secondary to hypertension. These data were compiled from our completed studies which formed the basis for this application. Thus, differential diagnoses can be made on these profiles and more importantly more specific clinical decision making and therapeutic strategies considered. Examples of clinical applications for this profile and how these would be utilized in clinical decision making was provided in the initial application.

TABLE 10

Differential Diagnosis of Systolic (Post-MI) or Diastolic (Hypertensive Heart Disease) Heart Failure*

| | Systolic HF | Diastolic HF |
|---|---|---|
| Plasma MMP/TIMP Profiles | | |
| MMP-2 | ↓ | ↓ |
| MMP-9 | ↑ | → |
| MMP-7 | → | → |
| MMP-13 | → | ↓ or ND |
| MMP-8 | ↑ | → |
| TIMP-1 | ↑ | ↑↑ |
| TIMP-2 | ↑ | ↑↑ |
| TIMP-4 | ↓ | ↑↑ |
| Plasma MMP/TIMP Ratios | | |
| MMP-9/TIMP-1 | ↑ | ↓ |
| MMP-9/TIMP-2 | ↑ | ↓ |
| MMP-9/TIMP-4 | ↑ | ↓ |

E. References

Bigg H F, Morrison C J, Butler G S, Bogoyevitch M A, Wang Z, Soloway P D, et al. Tissue inhibitor of metalloproteinase-4 inhibits but does not support the activation of gelatinase A via efficient inhibition of membrane type 1-matrix metalloproteinase. Cancer Res 2001; 61(9): 3610-8.

Bradham W S, Gunasinghe H, Holder J R, Multani M M, Killip D, Anderson M, et al. Release of matrix metalloproteinases following alcohol septal ablation in hypertrophic obstructive cardiomyopathy. JACC 2002; 40(12): 2165-73.

Brew K, Dinakarpandian D, Nagase H. Tissue inhibitors of metalloproteinases: evolution, structure and function. Biochimica et Biophysica Acta. 2000; 1477:267-283.

Caterina N C M, Windsor L J, Bodden M K, Yermovsky A E, Taylor K B, Birkendal-Hanson H, et al. Glycosylation and $NH_2$-terminal domain mutant of tissue inhibitor of metalloproteinases-1 (TIMP-1). Biochem Biophys Acta 1998; 1388: 21-34.

Chapman R E, Spinale F G. Extracellular protease activation and unraveling of the myocardial interstitium: critical steps toward clinical applications. Am. J. Physiol. 2004; 286; H1-H10.

Chobanian A V, Bakris G L, Black H R, Cushman W C, Green L A, Izzo J L Jr, Jones D W, Materson B J, Oparil S, Wright J T Jr, Roccella E J; National Heart, Lung, and Blood Institute Joint National Committee on Prevention, Detection, Evaluation, and Treatment of High Blood Pressure; National High Blood Pressure Education Program Coordinating Committee. The Seventh Report of the Joint National Committee on Prevention, Detection, Evaluation, and Treatment of High Blood Pressure: the JNC 7 report. JAMA. 2003; 289:2560-72.

Creemers E E J M, Cleutjens J P M, Smits J F M, Daemen M J A P. Matrix metalloproteinase inhibition after myocardial infarction. A new approach to prevent heart failure? Circulation Res 2001; 89; 201-210.

Dennis J W, Granovsky M, Warren C E. Protein glycosylation in development and disease. BioEssays 1999; 21: 412-421.

Deschamps A M, Apple K A, Leonardi A H, McLean J E, Yarbrough W M, Stroud R E, Clark L L, Sample J A, Spinale F G. Myocardial interstitial matrix metalloproteinase activity is altered by mechanical changes in LV load: interaction with the angiotensin type 1 receptor. Circ Res. 2005; 27; 96:1110-8.

Devereux R B, Alonso D R, Lutas E M, Gottlieb G J, Campo E, Sachs I, Reichek N. Echocardiographic assessment of left ventricular hypertrophy: comparison to necropsy findings. Am J Cardiol. 1986; 57:450-8.

Diez J, Querejeta R, Lopez B, Gonzalez A, Larman M, Martinez Ubago J L. Losartan-dependent regression of myocardial fibrosis is associated with reduction of left ventricular chamber stiffness in hypertensive patients. Circulation. 2002; 105:2512-2517.

Douglas D A, Shi E, Sang Q A. Computational sequence analysis of the tissue inhibitor of metalloproteinase family. J Protein Chem 1997, 16: 237-255.

Edwards D R, Beaudry P P, Laing T D, Kowal V, Leco K J, Leco P A, Lim M S. The roles of tissue inhibitors of metalloproteinases in tissue remodeling and cell growth. Int J Obes 1996:20: S9-S15.

Galis Z S, Khatri J J. Matrix metalloproteinases in vascular remodeling and atherogenesis: the good, the bad and the ugly. Circ Res 2002; 90: 251-62.

Goffin F, Munaut C, Frankenne F, Perrier D'Hauterive S, Beliard A, Fridman V, et al. Expression pattern of metalloproteinases and tissue inhibitor of matrix metalloproteinases in cycling human endometrium. Biol Reprod 2003.

Gomez D E, Alonso D F, Yoshiji H, Thogeirsson U P. Tissue inhibitor of metalloproteinases: structure, regulation, and biological functions. EJCB 1997, 74: 111-112.

Greene J, Wang M, Liu Y E, Raymond L A, Rosen C, Shi Y E. Molecular cloning and characterization of human tissue inhibitor of metalloproteinase 4. J Biol Chem 1996; 271: 30375-30380.

Gunasinghe S K, Ikonomidis J S, Spinale F G. Contributory role of matrix metalloproteinases in cardiovascular remodeling. Cardiovasc Heamat Disorders, 1(2) 75-91, 2001

Nagase H. Activational mechanisms of matrix metalloproteinases. Biological Chemistry 1997; 378: 151-160.

Hojo Y, Ikeda U, Ueno S, Arakawa H, Shimada K. Expression of matrix metalloproteinases in patients with acute myocardial infarction. Jpn Circ J 2001; 65: 71-75.

Joffs C, Himali R, Gunasinghe R S, Multani M M, Dorman B H, Kratz J M, Crumbley A J III, Crawford F A Jr., Spinale F G. Cardiopulmonary bypass induces the synthesis and release of matrix metalloproteinases. Ann Thorac Surg. 2001; 71:1518-23.

Kai H, Ikeda H, Yusakawa H, Kai M, Seki Y, Kuwahara F, Ueno T, Sugi K, Imaizumi T. Peripheral blood levels of matrix metalloproteinases-2 and -9 are elevated in patients with acute coronary syndromes. J Am Coll Cardiol 1998; 32: 368-372.

Kenchaiah S, Pfeffer M A. Cardiac remodeling in systemic hypertension. Med Clin North Am. 2004; 88:115-130.

Laviades C, Varo N, Fernandes J, Mayor G, Gil M J, Monreal I, Diez J. Abnormalities of the extracellular degradation of collagen type I in essential hypertension. Circulation. 1998; 98:535-540.

Levy D, Larson M G, Vasan R S, Kannel W B, Ho K K L: The progression from hypertension to congestive heart failure. JAMA. 1996; 275: 1557-1562.

Li Y Y, Feldman A M, Sun Y, McTieman C F. Differential expression of tissue inhibitors of metalloproteinases in the failing human heart. Circulation 1998, 98: 1728-1734.

Li Y Y, Feng, McTierman C F, Pei W, Moravec C S, Wang P, et al. Downregulation of matrix metalloproteinases and reduction in collagen damage in the failing human heart after support with left ventricular assist devices. Circulation 2001; 104: 1147-52.

Lindsay M M, Maxwell P, Dunn F G: TIMP-1. A marker of left ventricular diastolic dysfunction and fibrosis in hypertension. Hypertension. 2002; 40: 136-141.

Lindsey M L, Mann D L, Entman M L, Spinale F G. Extracellular matrix remodeling following myocardial injury. Ann Med. 2003; 35:316-316.

Li-Saw-Hee F L, Edmunds E, Blann A D, Beevers D G, Lip G Y H: Matrix metalloproteinase-9 and tissue inhibitor metalloproteinase-1 levels in essential hypertension. Relationship to left ventricular mass and anti-hypertensive therapy. Int J Cardiol. 2000; 75:43-47.

Liu Y E, Wang M, Greene J, Su J, Ullrich S, Li H, Sheng S, Alexander P, Sang Q A, Shi Y E. Preparation and characterization of recombinant tissue inhibitor of metalloproteinase 4. Am Soc Biochem Mol Biol 1997, 272: 20479-20483.

Lloyd-Jones D M, Larson M G, Leip E P, Beiser A, D'Agostino R B, Kannel W B, Murabito J M, Vasan R S, Benjamin E J, Levy D. Lifetime risk for developing congestive heart failure. The Framingham Study. Circulation. 2002; 106:3068-3072.

Lopez B, Gonzalez A, Varo N, Laviades C, Querejeta R, Diez: J: Biochemical assessment of myocardial fibrosis in hypertensive heart disease. Hypertension. 2001b; 38:1222-1226.

Lopez B, Querejeta R, Varo N, Gonzalez A, Larman M, Ubago J L M, Diez J: Usefulness of serum carboxy-terminal propeptide of procollagen type I in assessment of the cardioreparative ability in antihypertensive treatment in hypertensive patients. Circulation. 2001a; 104:286-291.

Maron B J. Hypertrophic cardiomyopathy: a systematic review. JAMA 2002; 13: 287(1308-1320).

Nagueh S F, Lakkis N M, Middleton K J, Killip D, Zoghbi W A, Quinones M A, Spencer S H 3rd. Changes in left ventricular diastolic function 6 months after nonsurgical septal reduction therapy for hypertrophic obstructive cardiomyopathy. Circulation 1999: 99:344-347.

Nagueh S F, Lakkis N M, Middleton K J, Killip D, Zoghbi W A, Quinones M A, Spencer S H 3rd. Changes in left ventricular filling and left atrial function six months after nonsurgical septal reduction therapy for hypertrophic obstructive cardiomyopathy. J Am Coll Cardiol 1999; 34: 1123-1128.

Nagueh S F, Mikati I, Kopelen H A, Middleton K J, Quinones M A, Zoghbi W A: Doppler estimation of left ventricular filling pressure in sinus tachycardia. A new application of tissue Doppler imaging. Circulation. 1998; 98:1644-1650.

Nuegh S F, Stevenson S J, Lakkis N M, Killip D, Perez-Verdia A, Entman M L, et al. Decreased expression of tumor necrosis factor-alpha and regression of hypertrophy after nonsurgical septal reduction therapy for patients with hypertrophic obstructive cardiomyopathy. Circulation 2001; 103(14): 1844-50.

Parsons S L, Watson S A, Brown P D, Collins H M, Steele R J C. Matrix metalloproteinases. Brit J Surg 1997; 84:160-166.

Peterson J T, Li H, Dilon L, Bryant J W. Evolution of matrix metalloproteinase and tissue inhibitor expression during heart failure progression in the infracted rat. Cardiovas Res 2000; 46: 307-315.

Radomski A, Juraz P, Sanders E J, Overall C M, Biggs H F, Edwards D R, et al. Identification, regulation and role of tissue of tissue inhibitor of metalloproteinases-4 (TIMP-4) in human platelets. Br J Pharmaco 2002; 137(8): 1130-1338.

Sahn D J, DeMaria A, Kisslo J, Weyman A. Recommendations regarding quantitation in M-mode echocardiography: results of a survey of echocardiographic measurements. Circulation. 1978; 58: 1072-1083.

Schillaci G. Pasqualini L, Verdecchia P, Vaudo G, Marchesi S, Porcellati C, De Simone G, Mannarion E. Prognostic significance of left ventricular diastolic dysfunction in essential hypertension. J Am Coll Cardiol. 2002; 39:2005-2011.

Schiller N B, Shah P M, Crawford M, DeMaria A, Devereux R, Feigenbaum H, Gutgesell H, Reichek N, Sahn D, Schnittger I. Recommendations for quantitation of the left ventricle by two-dimensional echocardiography. American Society of Echocardiography Committee on Standards, Subcommittee on Quantitation of Two-Dimensional Echocardiograms. J Am Soc Echocardiography. 1989; 2: 358-367.

Sharp P S, Rainbow S, Mukherjee S. Serum levels of low molecular weight advanced glycation end products in diabetic subjects. Diabet Med 2003; 20(7): 575-9.

Spencer W H 3rd, Roberts R. Alcohol septal ablation in hypertrophic obstructive cardiomyopathy: the need for a registry. Circulation 2000; 102: 600-01.

Spinale F G, Coker M L, Heung L J, Bond B R, Gunasinghe H R, Etoh T, et al. A matrix metalloproteinase induction/activation system exists in the human left ventricular myocardium and is upregulated in heart failure. Circulation 2000; 102; 1944-1949.

Spinale, F G. Matrix metalloproteinases. Regulation and dysregulation in the failing heart. Circ. Res. 2002; 90:520-530.

Steinberg T H, Pretty On Top K, Berggren K N, Kemper C, Jones L, Diwu Z, et al. Rapid and simple single nanogram detection of glycoproteins in polyacrylamide gels on electroblots. Proteomics 2001; 1(7): 841-55.

Stroud R E, Deschamps A M, Lowry A S, Hardin A E, Mukherjee R, Lindsey M L, Ramamoorthy S, Zile M R, Spencer W H, Spinale F G. Plasma monitoring of the myocardial specific tissue inhibitor of metalloproteinase-4 after alcohol septal ablation in hypertrophic obstructive cardiomyopathy. J Card Fail. 2005; 11:124-30

Tayebjee M H, Lim H S, Nadar S, MacFadyen R J, Lip G Y. Tissue inhibitor of metalloproteinse-1 is a marker of diastolic dysfunction using tissue doppler in patients with type 2 diabetes and hypertension. Eur J Clin Invest. 2005; 35:8-12.

Tayebjee M H, Nadar S, Blann A D, Gareth Beevers D, MacFadyen R J, Lip G Y. Matrix metalloproteinase-9 and tissue inhibitor of metalloproteinase-1 in hypertension and their relationship to cardiovascular risk and treatment: a substudy of the Anglo-Scandinavian Cardiac Outcomes Trial (ASCOT). Am J. Hypertens. 2004; 17:764-9.

Tayebjee M H, Nadar S K, MacFadyen R J, Lip G Y. Tissue inhibitor of metalloproteinase-1 and matrix metalloproteinase-9 levels in patients with hypertension Relationship to tissue Doppler indices of diastolic relaxation. Am J. Hypertens. 2004; 17:770-4.

Timms, P M, Wright A, Maxwell P, Campbell S, Dawnay A B, Srikanthan V. Plasma tissue inhibitor of metalloproteinase-1 levels are elevated in essential hypertension and related to left ventricular hypertrophy. Am J. Hyper. 2002: 15:269-272.

Tsuruda T, Costello-Boerrigter L C, Burnett J C Jr. Matrix metalloproteinases: pathways of induction by bioactive molecules. Heart Fail Rev. 2004; 9:53-61.

Vu T H, Werb Z. Matrix metalloproteinases: effectors of development and normal physiology. Genes Dev 2000; 14:2123-2133 Gross J, Lapiere C M. Collagenolytic activity in amphibian tissues: a tissue culture assay. Proc Natl Acad Sci USA 1962; 48: 1014-1022.

Wachtell, K, Smith G, Gerdts E, Dahlof B, Nieminen M S, Papademetriou V, Bella J N, Ibsen H, Rokkedal J, Devereux R B. Left ventricular filling patterns in patients with systemic hypertension and left ventricular hypertrophy (The Life Study). Am J. Cardiol. 2000; 85:466-472.

Wassef M, Baxter B T, Chisholm R L, Dalman R L, Fillinger M F, Heinecke J, et al. Pathogenesis of abdominal aortic aneurysms: a multidisciplinary research program supported by the National Heart, Lung, and Blood Institute. J Vas Surg 2001; 34: 730-8.

Weber K T, Brilla C G. Pathological hypertrophy and cardiac interstitium. Fibrosis and renin-angiotensin-aldosterone system. Circulation 1991; 83: 1849-65.

Weber K T, Sun Y, Guarda E: Structural remodeling in hypertensive heart disease and the role of hormones. Hypertension. 1994; 23:869-877.

Wilson E M, Gunasinghe H R, Coker M L, Sprunger P, Lee-Jackson D, Bozkurt B, Deswal A, Mann D L, Spinale F G. Plasma matrix metalloproteinase and inhibitor profiles in patients with heart failure. J Cardiac Failure. 2002; 8:390-398.

Woessner J F, Nagase H. Activation of the zymogen forms of MMPs. In: Matrix metalloproteinases and TIMPs. Oxford University Press, Oxford UK, 2000 pp 72-86.

Yarbrough W M, Mukherjee R, Escobar P, Mingoia J T, Sample J A, Hendrick J W, Dowdy K B, McLean J E, Lowry A S, O'Neil T P, Spinale F G. Selective targeting and timing of matrix metalloproteinase inhibition in post-myocardial infarction remodeling. Circulation. 2003; 108: 1753-1759.

Yasmin, Wallace S, McEniery C M, Dakham Z, Pusalkar P, Maki-Petaja K, Ashby M J, Cockcroft J R, Wilkinson I B. Matrix metalloproteinase-9 (MMP-9), MMP-2, and serum elastase activity are associated with systolic hypertension and arterial stiffness. Arterioscler Thromb Vasc Biol. 2005; 25:372.

Zervoudaki A, Economou E, Stefanadis C, Pitsavos C, Tsioufis K, Aggeli C, Vasiliadou K, Toutouza M, Toutouzas P: Plasma levels of active extracellular matrix metalloproteinases 2 and 9 in patients with essential hypertension before and after antihypertensive treatment. J Hum Hypertens. 2003; 17:119-124.

Zile M R, Brutsaert D L: New concepts in diastolic dysfunction and diastolic heart failure. Part I: Diagnosis, prognosis, measurements of diastolic function. Circulation. 2002; 105:1487-1393.

Zile M R, Brutsaert D L: New concepts in diastolic dysfunction and diastolic heart failure. Part II: Causal mechanisms and treatment. Circulation. 2002; 105:1503-1508.

We claim:

1. A method of predicting diastolic heart failure in a subject, comprising measuring the amount of one or more MMPs and TIMPs in a body fluid from the subject, wherein the one or more MMPs and TIMPs comprise TIMP-4, wherein the body fluid is blood, plasma, or serum, wherein the amount of one or more of the one or more MMPs and TIMPs indicates the presence of diastolic heart failure or a risk for developing diastolic heart failure, wherein an increased amount of TIMP-4 indicates the presence of diastolic heart failure or a risk for developing diastolic heart failure.

2. The method of claim 1, wherein an amount of TIMP-4 that is greater than the normal value is detected in a body fluid from the subject.

3. The method of claim 2, wherein the amount of TIMP-4 is at least about 50% greater than the normal value.

4. The method of claim 1, wherein the body fluid is blood.

5. The method of claim 1, wherein the body fluid is plasma.

6. The method of claim 1, wherein the amount of TIMP-4 is at least about 50% greater than the normal value.

7. The method of claim 1, wherein the amounts of MMP-2 and MMP-8 are also measured in the body fluid from the subject.

8. The method of claim 1, wherein the one or more MMPs and TIMPs does not comprise TIMP-1.

9. The method of claim 1, wherein the one or more MMPs and TIMPs consist of TIMP-4 and one or more of MMP-2, MMP-7, MMP-9, MMP-11, MMP-13, MMP-14, MMP-15, MMP-16, MMP-17, MMP-19, MMP-23, MMP-26, TIMP-2, and TIMP-3.

10. The method of claim 1, wherein the subject is hypertensive.

11. The method of claim 1, wherein the subject exhibits left ventricular hypertrophy.

12. A method of predicting diastolic heart failure in a subject, comprising measuring the amount of one or more MMPs and TIMPs in a body fluid from the subject, wherein the one or more MMPs and TIMPs does not comprise TIMP-1, wherein the body fluid is blood, plasma, or serum, wherein the amount of one or more of the one or more MMPs and TIMPs indicates the presence of diastolic heart failure or a risk for developing diastolic heart failure.

13. The method of claim 12, wherein the amount of TIMP-4 is measured in the body fluid from the subject, and wherein the amount of TIMP-4 indicates the presence of diastolic heart failure or a risk for developing diastolic heart failure.

14. The method of claim 13, wherein an amount of TIMP-4 that is greater than the normal value is detected in a body fluid from the subject.

15. The method of claim 14, wherein the amount of TIMP-4 is at least about 50% greater than the normal value.

* * * * *